(12) United States Patent
Gil et al.

(10) Patent No.: US 8,592,446 B2
(45) Date of Patent: **\*Nov. 26, 2013**

(54) [1,10]-PHENANTHROLINE DERIVATIVES FOR THE TREATMENT OF NEURODEGENERATIVE OR HAEMATOLOGICAL DISEASES

(75) Inventors: Ana Martinez Gil, Tres Cantos (ES); Ana Castro Morera, Tres Cantos (ES); Miguel Medina Padilla, Tres Cantos (ES); Jorge Sanchez-Quesada, Tres Cantos (ES); Mercedes Alonso Cascon, Tres Cantos (ES); Laura Rubio Arrieta, Tres Cantos (ES); Esther Garcia Palomero, Tres Cantos (ES); Paola Usan Egea, Tres Cantos (ES)

(73) Assignee: Noscira, S.A., Tres Cantos (Madrid) (ES)

( * ) Notice: Subject to any disclaimer, the term of this patent is extended or adjusted under 35 U.S.C. 154(b) by 592 days.

This patent is subject to a terminal disclaimer.

(21) Appl. No.: 12/664,130

(22) PCT Filed: Jun. 11, 2008

(86) PCT No.: PCT/EP2008/057319
§ 371 (c)(1),
(2), (4) Date: Mar. 10, 2010

(87) PCT Pub. No.: WO2008/152068
PCT Pub. Date: Dec. 18, 2008

(65) Prior Publication Data
US 2010/0240692 A1    Sep. 23, 2010

(30) Foreign Application Priority Data
Jun. 11, 2007   (EP) .................................... 07380167

(51) Int. Cl.
*C07D 221/16* (2006.01)
*C07D 487/04* (2006.01)
*A61K 31/4375* (2006.01)

(52) U.S. Cl.
USPC .......................................... 514/290; 546/80

(58) Field of Classification Search
USPC ........................................... 546/80; 514/290
See application file for complete search history.

(56) References Cited

FOREIGN PATENT DOCUMENTS

PL             76345 B       6/1975

OTHER PUBLICATIONS

Chemical Abstract Service (CAPLUS) Accession No. 1971:529695 for Journal Article by Mlochowski, J. et al., 'Synthesis of phenanthroline analogs of cerulomycin', Roczniki Chemii, 1971, p. 803-809, vol. 45 (Abstract Only), 1971, p. 1, Publisher: Chemical Abstracts Service.
"Chemical Abstract Service (CAPLUS) Accession No. 1976:421321 for Polish Patent PL 76 345 B to Mlochowski, J. et al., entitled '1,10-Phenanthroline Derivatives'" (Abstract Only), 1976, p. 1, Publisher: Chemical Abstracts Service.
"Chemical Abstract Service (CAPLUS) Accession No. 1977:43584 for Journal Article by Mlochowski, J. et al., entitled 'Synthesis, structure, and reactivity of phenanthrolines', Prace Naukowe Instytutu Chemii Organicznej I Fizycznej Politechniki Wroclawskiej, 9, 1-133, ISSN: 0370-081X, 1975" (Abstract Only), 1977, p. 1, Publisher: Chemical Abstracts Service.
Cherny, R. et al. , "Chelation and Intercalation: Complementary Properties in a Compound for the Treatment of Alzheimer's Disease", "Journal of Structural Biology", 2000, pp. 209-216, vol. 130.
Gaeta, A. et al. , "The crucial role of metal ions in neurodegeneration; the basis for a promising therapeutic strategy", "British Journal of Pharmacology", Dec. 2005, pp. 1041-1059, vol. 146.
Mlochowski, J. et al. , "Synthesis of Phenanthroline Analogues of Caerulomycin", "Roczniki Chemii", 1971, p. 803, vol. 45.

*Primary Examiner* — Rita Desai
(74) *Attorney, Agent, or Firm* — Hultquist, PLLC; Steven J. Hultquist

(57) ABSTRACT

The present invention relates to a new family of [1,10]-phenantroline derivatives of formula (I), which are useful for the treatment or profilaxis of a neurodegenerative or haematological disease or condition, their use as a medicament, especially for treating a treatment neurodegenerative or haematological disease or condition, and a pharmaceutical composition comprising the compounds.

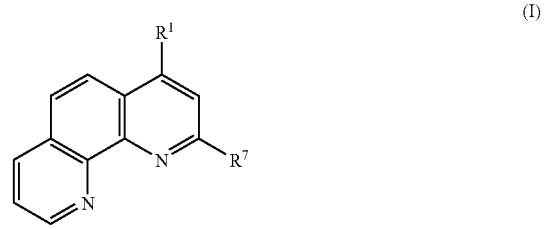

(I)

12 Claims, 8 Drawing Sheets

[1,10]-PHENANTHROLINE DERIVATIVES FOR THE TREATMENT OF NEURODEGENERATIVE OR HAEMATOLOGICAL DISEASES

CROSS REFERENCE TO RELATED APPLICATIONS

This application is a U.S. national phase under the provisions of 35 U.S.C. §371 of International Application No. PCT/EP08/57319 filed Jun. 11, 2008, which in turn claims priority of European Patent Application No. 07380167.2 filed Jun. 11, 2007. The disclosures of such international application and European priority application are hereby incorporated herein by reference in their respective entireties, for all purposes.

FIELD OF THE INVENTION

The present invention relates to the use of some [1,10]-phenanthroline derivatives for the treatment and/or prophylaxis of a neurodegenerative or haematological disease or condition, particularly Alzheimer's disease (AD). Additionally, there is provided new [1,10]-phenanthroline derivatives, a process for preparing such compounds and pharmaceutical compositions comprising them.

BACKGROUND OF THE INVENTION

AD and Parkinson's disease (PD) are the most frequent progressive neurodegenerative diseases affecting millions of people in the world. Because a significant percentage of patients share common clinical and pathological symptoms from both entities, this seems to indicate the existence of a common pathological mechanism.

Oxidative stress is known to be involved in many diseases, including atherosclerosis, Parkinson's disease and AD, and may be also important in ageing.

Reactive oxygen species (ROS), such as oxygen radical superoxide ($O_2^-$) or hydrogen peroxide ($H_2O_2$), are produced during normal metabolic processes and perform several useful functions (Reactive oxygen species and the central nervous system, Halliwell B., *J. Neurochem.;* 1992, 59 859: 1609-1623). Cells are provided with several mechanisms to control levels of these oxidative agents, for instance, superoxide dismutase (SOD), glutathione or vitamin E. In normal physiological conditions, a balance between ROS and these anti-oxidative mechanisms exists. An excessive production of ROS and a loss of efficiency of the anti-oxidative defences can lead to cellular oxidative stress and thus to pathological conditions in cells and provoke tissue damage. This event seems to occur more dramatically in neurons, because of their high rate of metabolic activity, and thus seems to be related to a series of degenerative processes, diseases and syndromes, for example, AD, PD, amyotrophic lateral sclerosis (ALS) and schizophrenia (Glutathione, oxidative stress and neurodegeneration, Schulz et al., *Eur. J. Biochem.;* 2000, 267, 4904-4911). Also other diseases or pathological conditions have been related to oxidative stress, such as Huntington's Disease (Oxidative damage in Huntington's disease, Segovia J. and Pérez-Severiano F, *Methods Mol. Biol.;* 2004; 207: 321-334), brain injuries, such as stroke and ischemia, (Oxidative Stress in the Context of Acute Cerebrovascular Stroke, El Kossi et al., *Stroke;* 2000; 31: 1889-1892), diabetes (Oxidative stress as a therapeutic target in diabetes: revisiting the controversy, Wiernsperger N F, *Diabetes Metab.;* 2003; 29, 579-85), multiple sclerosis (The role of oxidative stress in the pathogenesis of multiple sclerosis: the need for effective anti-oxidant therapy, Gilgun-Sherki Y. et al., *J. Neurol.;* 2004; 251 (3): 261-8), epilepsy (Oxidative injury in epilepsy: potential for antioxidant therapy?, Costello D. J. and Delanty N., Expert. *Rev. Neurother.;* 2004; 4(3):541-553), atherosclerosis (The oxidative stress hypothesis of atherogenesis, Iuliano L., *Lipids;* 2001; 36 suppl: S41-44), Friedreich's Ataxia (Oxidative stress mitochondrial dysfuntion and cellular stress response in Friedreich's ataxia, Calabrese et al., *J. Neurol. Sci.;*2005) and heart failure (Oxygen, oxidative stress, hypoxia and heart failure, Giordano F. J., *J. Clinic. Invest.;* 2005; 115 (3): 500-508). Treatments that lead to an enhancement of the anti-oxidative mechanisms may slow down the progression of some of the mentioned diseases.

Another type of cellular stress is the endoplasmic reticulum (ER) stress. The ER is an intracellular organelle represented by an extensive network formed by cisternae and microtubules and which extends from the nuclear envelope to the cell surface in all eukaryotic cells. ER plays several vital functions: the rough ER is the place for protein synthesis and postranslational changes for the correct folding of proteins, ER is the common transport route to deliver proteins to their proper destination within the cell and it is also a $Ca^{2+}$ reservoir. Disturbances in the function of ER lead to accumulation of unfolded proteins within the ER, inducing a condition generally referred to as ER stress. These disturbances can be caused not only by biochemical imbalance but also by disturbance in the ER $Ca^{2+}$ homeostasis. Some studies (Glycogen synthase kinase 3β (GSK3β) mediates 6-hydroxydopamine-induced neuronal death, Chen et al., *FASEB J.* 2004;18(10): 1162-4) demonstrate that ER stress activates the enzyme glycogen synthase kinase 3β, an enzyme involved in the neurodegenerative process occurred in patients with AD.

The catecholaminergic neurotoxin 6-hydroxydopamine (6-OHDA) is formed endogenously in patients suffering from Parkinson's disease. 6-OHDA has two ways of action: it easily forms free radicals and it is a potent inhibitor of the mitochondrial respiratory chain complexes I and IV. 6-hydroxydopamine (6-OHDA) models are used to produce a broad spectrum of neurochemical and behavioural deficits characterising DA degeneration in humans, specially for PD (e.g. Glinka Y et al, "Mechanism of 6-hydroxydopamine neurotoxicity", J Neural Transm Suppl. 1997;50:55-66; Willis G L et al, "The implementation of acute versus chronic animal models for treatment discovery in Parkinson's disease" Rev Neurosci. 2004;15(1):75-87).

A common sign of neurodegenerative diseases is the accumulation and deposits of misfolded proteins which affect several signalling pathways which lead finally to neuronal death. Some authors (ER stress and neurodegenerative diseases, Lindholm et al., *Cell Death and Differentiation;* 2006; 13: 385-392) consider that ER stress is related to several neurodegenerative diseases such as, PD, AD, ALS, and transmissible spongiform encephalopaties (TSEs).

In view of the above, an interesting approach for developing new pharmaceutical compounds for treating neurodegenerative diseases may be designing compounds which inhibit cellular oxidative stress.

Amyloid beta (Aβ) is a peptide that is the main constituent of amyloid plaques in the brains of AD patients. Similar plaques appear in some variants of Lewy body dementia and in inclusion body myositis, a muscle disease. Aβ also forms aggregates coating cerebral blood vessels in cerebral amyloid angiopathy.

Aβ is formed after sequential cleavage of the amyloid precursor protein (APP) by the β- and γ-secretases. Either $Aβ_{42}$ or $Aβ_{40}$ are produced depending on where the cleavage occurs. APP is a transmembrane glycoprotein. Autosomal-dominant mutations in APP cause hereditary early-onset AD, likely as a result of altered proteolytic processing. Increases in total Aβ levels have been implicated in the pathogenesis of both familial and sporadic AD [The American Journal of Pathology; Lue, L; 155(3):853-662 (1999)].

According to the "amyloid hypothesis", accepted by the majority of researchers, the plaques are responsible for the pathology of AD. Intra-cellular deposits of tau protein are also seen in the disease, and may also be implicated. The oligomers that form on the amyloid pathway, rather than the mature fibrils, may be the cytotoxic species.

Thus, the development of inhibitors of amyloid beta secretion are a current strategy to find treatments for diseases in which amyloidosis is involved, such as AD, PD, Huntington's disease, TSEs, Prion diseases, Creutzfeldt-Jakob disease and Bovine spongiform encephalopathy.

On the other hand, iron chelators are used to treat some kinds of haematological diseases, such as thalassaemia, anaemia, aplastic anaemia, myelodysplastic syndrome, diabetes, Diamond-Blackfan anaemia, sickle cell disease, hematologic disorders which require regular red cell transfusions, iron-induced cardiac dysfunction, and iron-induced heart failure.

Metals such as iron are capable of redox cycling in which a single electron may be accepted or donated by the metal. This action catalyzes reactions that produce reactive radicals and can produce reactive oxygen species. The most important reactions are probably Fenton's reaction and the Haber-Weiss reaction, in which hydroxyl radical is produced from reduced iron and hydrogen peroxide. The hydroxyl radical then can lead to modifications of amino acids (e.g. meta-tyrosine and ortho-tyrosine formation from phenylalanine), carbohydrates, initiate lipid peroxidation, and oxidize nucleobases. Most enzymes that produce reactive oxygen species contain one of these metals. The presence of such metals in biological systems in an uncomplexed form (not in a protein or other protective metal complex) can significantly increase the level of oxidative stress. Therefore, it is desirable that chelating ligands for the treatment of conditions according to the invention, show a preference towards Fe(II) rather than Fe(III).

Iron chelators deferoxamine and deferiprone, have been used in humans since the 1970s and the late 1980s, respectively, and lately a new drug, deferasirox has been used in humans. Deferoxamine has proven efficient in thalassemia major, sickle cell disease and other hematologic disorders for which hematologic disorders, but can only be administered subcutaneously [Blood; Neufeld, E. L., 107(9): 3436-3441 (2006)]. Deferasirox, approved in the US for chronic iron overload due to blood transfusions, has shown moderate to good success [Hematology; Cohen, A. R., 42-47 (2006)]. Combination therapy with deferiprone and deferoxamine is also being used.

However, side effects have been associated with the use of these drugs; deferiprone often causes gastrointestinal symptoms, erosive arthritis, neutropenia and in some cases agranulocytosis; deferiprone therapy requires weekly complete blood count and ancillary supplies for infusion, so close monitoring is required; deferoxamine presents gastrointestinal symptoms and joint pain and deferasirox is costly. Therefore there still remains a need for additional therapeutic iron chelators for use in these hematological diseases, produced and used with low cost and reduced side effects.

It is well known that phenanthroline derivatives exhibit good iron chelating properties. Some phenanthroline derivatives are shown in patent PL76345. It would be highly recommended to find new phenanthroline derivatives which can show improved properties in chelating iron metal in order to provide an enhanced capability for treating the haematological mentioned diseases.

SUMMARY OF THE INVENTION

The authors of the present invention have found a new family of compounds, namely [1,10]-phenanthroline derivatives, defined by formula (I) as detailed below, which encompasses the properties of protecting from oxidative stress, particularly from hydrogen peroxide-cell death and 6-hydroxydopamine-cell death, having a neuroprotective effect against Aβ toxicity, and inhibiting Aβ secretion. Surprisingly, the inventors have found that the compounds of the invention are capable of crossing the brain blood barrier. They may thus be useful for the treatment or prophylaxis of neurodegenerative diseases or conditions. In addition, these compounds are characterized for acting as specific iron (II) chelators and therefore they could also be used to treat haematological diseases.

Therefore, according to a first aspect, the present invention is directed to the use of a compound of formula (I):

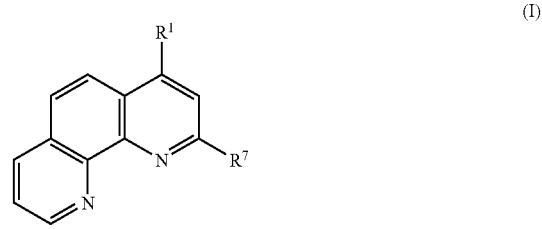

(I)

wherein $R^1$ is selected from —S—$R^3$, —O—$R^4$ and halogen;
$R^7$ is selected from —CH=N—$OR^8$ or —CHO;
$R^3$ and $R^4$ are independently selected from the group consisting of $C_1$-$C_6$ alkyl, $C_6$-$C_{15}$ aryl and heteroaryl, optionally substituted by $C_1$-$C_6$ alkyl, $C_6$-$C_{15}$ aryl, halogen, preferably by 1 to 6 halogen atoms, more preferably 1 to 3, —(C=O)$NR^5R^6$, —(C=O)$OR^5$,
$C_1$-$C_6$ alkoxy and/or —$NR^5R^6$,
$R^5$ and $R^6$ being independently selected from hydrogen and $C_1$-$C_6$ alkyl,
$R^8$ is selected from hydrogen and $C_1$-$C_6$ alkyl;
or any salt or solvate or stereoisomer or tautomer thereof,
in the preparation of a medicament for the treatment or prophylaxis of a neurodegenerative or haematological disease or condition.

Thus an aspect of the invention are the compounds of formula (I) as defined above for the treatment or prophylaxis of a neurodegenerative or haematological disease or condition.

The compounds of formula (I) may be used in biological assays wherein beta-amyloid secretion needs to be modulated. Therefore, in another aspect, the invention refers to the use of a compounds of formula (I) as defined above, or any salt or solvate thereof, as reagent for biological assays, preferably as a reactive for pharmacokinetic assays, blood brain barrier crossing assays, chelation assays, for essays on protection against hydrogen peroxide-induced cell death, protection against 6-OHDA-induced cell death, neuroprotection against Aβ toxicity and inhibiton of beta-amyloid secretion.

A further aspect of the invention refers to a method of treating or preventing a disease or condition, said method comprises administering to a patient in need of such a treatment a therapeutically effective amount of at least one compound of formula (I) as defined above, its salts, solvates, stereoisomers or tautomers thereof, or a pharmaceutical composition thereof.

According to a further aspect, the present invention is directed to a compound of formula (I):

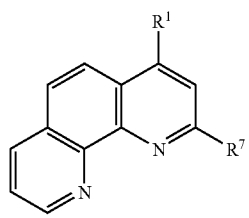

(I)

wherein $R^1$ is selected from —S—$R^3$, —O—$R^4$ and halogen;
$R^7$ is selected from —CH=N—$OR^8$ or —CHO;
$R^3$ and $R^4$ are independently selected from the group consisting of $C_1$-$C_6$ alkyl, $C_6$-$C_{15}$ aryl and heteroaryl, optionally substituted by $C_1$-$C_6$ alkyl, $C_6$-$C_{15}$ aryl, halogen, —(C=O)$NR^5R^6$, —(C=O)$OR^5$, $C_1$-$C_6$ alkoxy and/or —$NR^5R^6$,
$R^5$ and $R^6$ being independently selected from hydrogen and $C_1$-$C_6$ alkyl,
$R^8$ is selected from hydrogen and $C_1$-$C_6$ alkyl;
or any salt or solvate or stereoisomer or tautomer thereof, with the proviso that when $R^1$ is Cl, then $R^7$ is not —CHO.

Another aspect of the present invention refers to a pharmaceutical composition comprising at least one compound of formula (I) as defined above, its salts or solvates or stereoisomers or tautomers thereof, and at least one pharmaceutically acceptable carrier.

According to a further aspect, the present invention is directed to a compound of formula (I) as defined above, its salts, solvates or stereoisomers or tautomers thereof, for use as a medicament.

According to a further aspect, the present invention is directed to a process for the synthesis of the compounds of formula I, its salts or solvates or stereoisomers or tautomers thereof.

DETAILED DESCRIPTION OF THE INVENTION

Figure 1A:
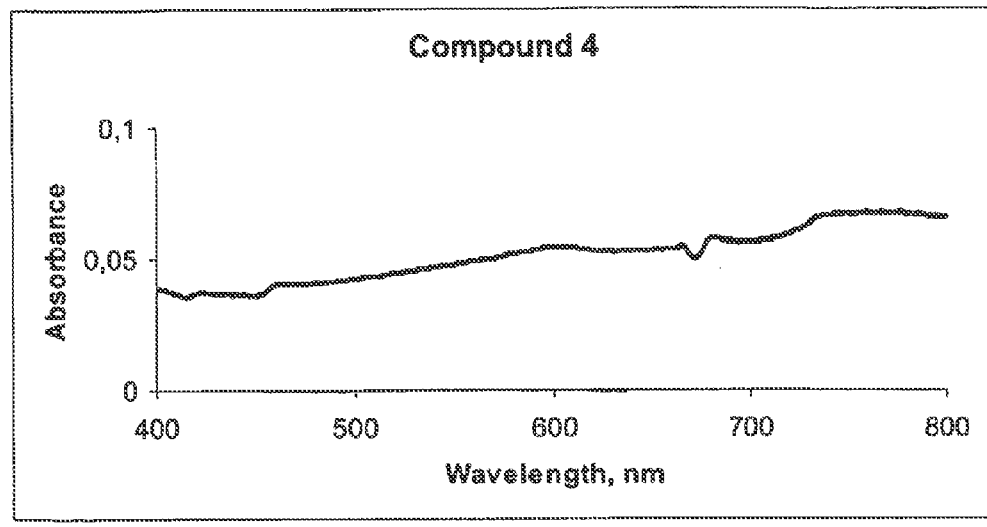
FIG. 1 is an absorbance spectrum of compounds 4, 7, 8 and 10 in absence and presence of Fe(III). PBS 10 mM, pH 7.4. Concentration of ligand and Fe(III), 200 µM.
Figure 1B:
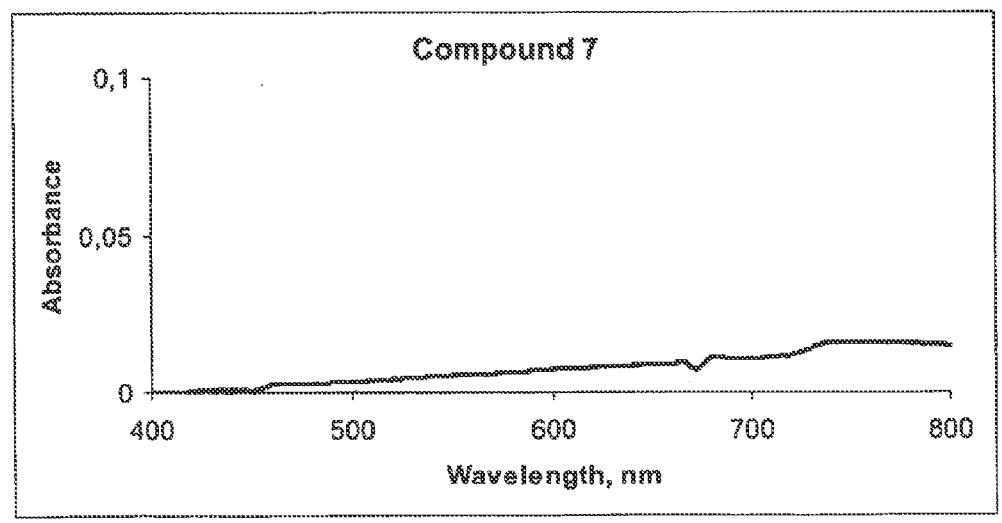
Figure 1C:
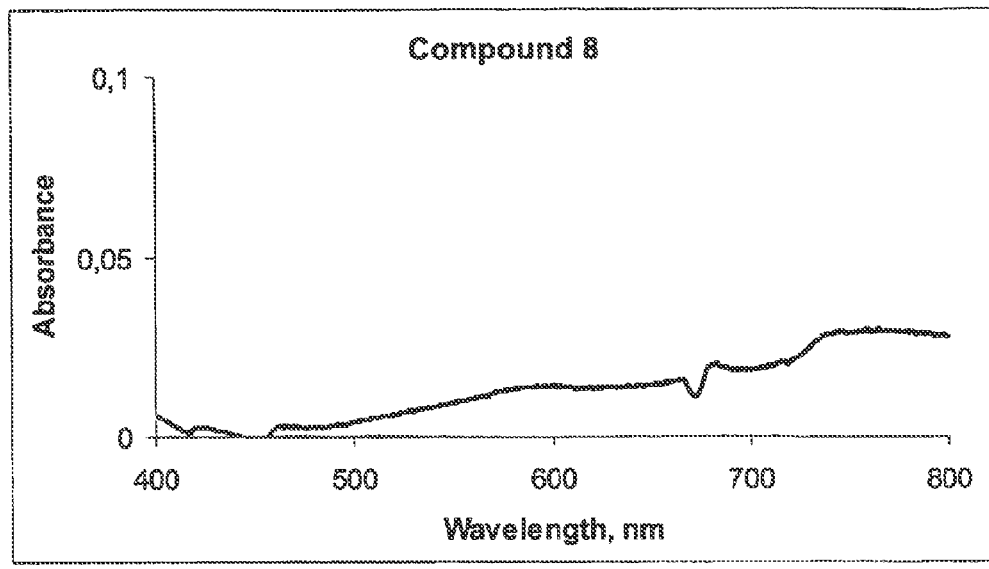
Figure 1D:
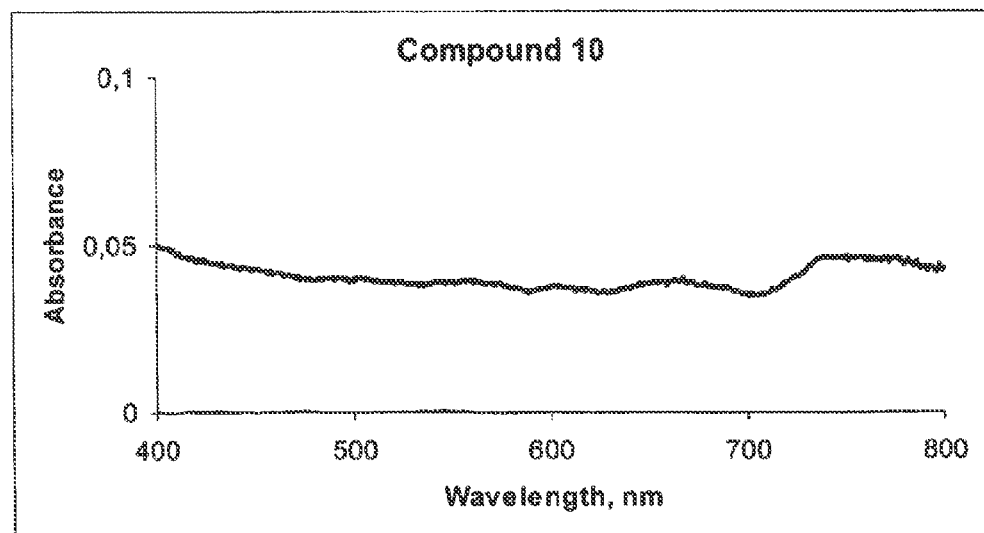
Figure 2:
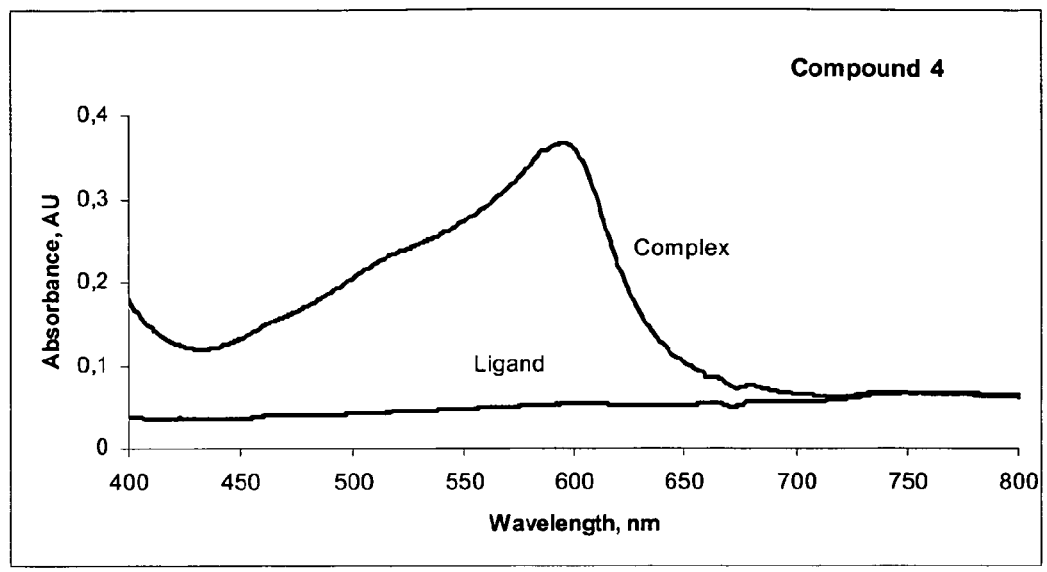
FIG. 2 is an absorbance spectrum of the complex Fe(II)-Compound 4. Concentration of Fe(II) and Compound 4, 200 µM, PBS 10 mM, pH 8.
Figure 3:
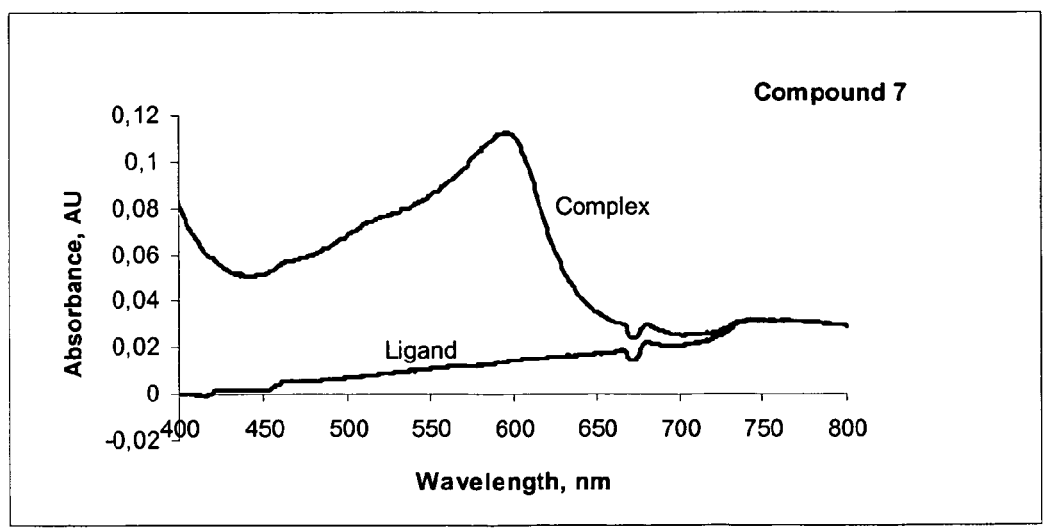
FIG. 3 is an absorbance spectrum of the complex Fe(II)-Compound 7. Concentration of Fe(II) and Compound 7, 400 µM, PBS 10 mM, pH 8.
Figure 4:
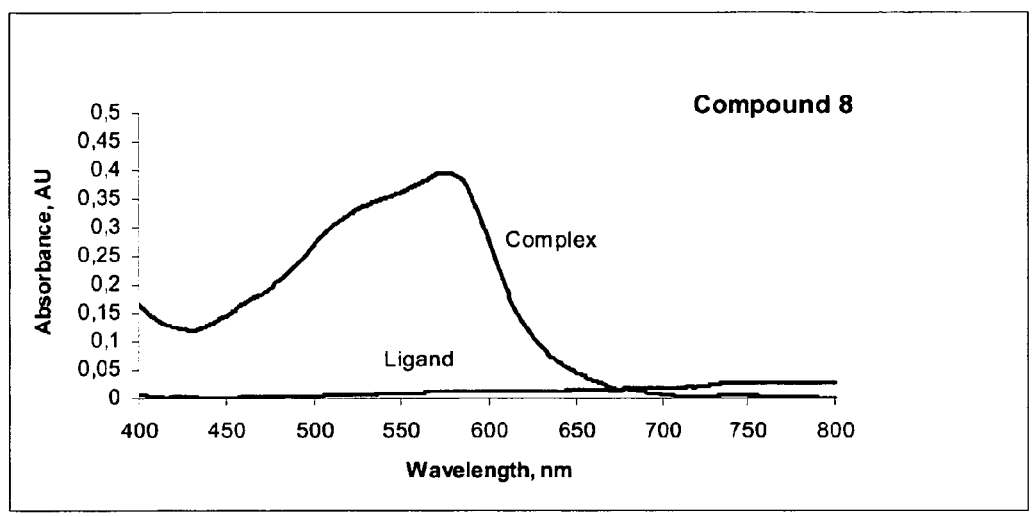
FIG. 4 is an absorbance spectrum of the complex Fe(II)-Compound 8. Concentration of Fe(II) and Compound 8, 200 µM, PBS 10 mM, pH 7.4.
Figure 5:
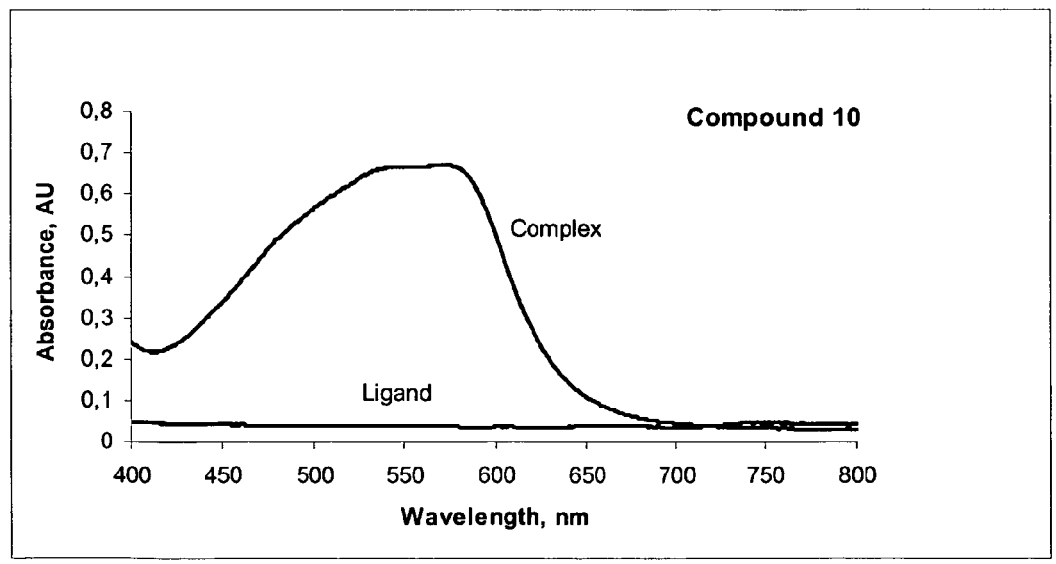
FIG. 5 is an absorbance spectrum of the complex Fe(II)-Compound 10. Concentration of Fe(II) and Compound 10, 100 µM, PBS 10 mM, pH 7.4.

In the above definition of compounds of formula (I) the following terms have the meaning indicated:

"$C_1$-$C_6$ Alkyl" refers to a linear or branched hydrocarbon chain radical consisting of carbon and hydrogen atoms, containing no unsaturation, having one to six carbon atoms, preferably one to three, and which is attached to the rest of the molecule by a single bond, e. g., methyl, ethyl, n-propyl, i-propyl, n-butyl, t-butyl, n-pentyl, etc.

"$C_1$-$C_6$ alkoxy" refers to a radical of the formula —$OR_a$ where $R_a$ is a "$C_1$-$C_6$ alkyl" radical as defined above, e. g., methoxy, ethoxy, propoxy, etc.

"Halogen" refers to bromo, chloro, iodo or fluoro.

"Aryl" refers to an aromatic hydrocarbon radical having 6 to 15, preferably 6 to 10 carbon atoms such as phenyl or naphthyl.

"Heteroaryl" refers to a stable 3- to 15-membered ring system wherein at least one of the rings is aromatic, and which consists of carbon atoms and from one to five heteroatoms, preferably one to three, selected from the group consisting of nitrogen, oxygen, and sulphur, preferably a 4- to 8-membered ring with one or more heteroatoms, more preferably a 5-or 6-membered ring with one or more heteroatoms, preferably one to three. For the purposes of this invention, the heteroaryl may be a monocyclic, bicyclic or tricyclic ring system, which may include fused ring systems; and the nitrogen, carbon or sulfur atoms in the heteroaryl radical may be optionally oxidised; the nitrogen atom may be optionally quaternized; Examples of such heteroaryles include, but are not limited to thiazol, thiadiazol, benzimidazole, benzothiazole, furan, isothiazole or imidazole.

Uses of compounds of formula (I)

According to one embodiment, the invention is directed to the use of a compound of formula (I), wherein
$R^1$ is selected from —S—$R^3$, —O—$R^4$ and halogen;
$R^7$ is selected from —CH=N—$OR^8$ or —CHO;
$R^3$ and $R^4$ are independently a $C_1$-$C_6$ alkyl, optionally substituted by $C_1$-$C_6$ alkoxy and/or —$NR^5R^6$,
$R^5$ and $R^6$ being independently selected from hydrogen and $C_1$-$C_6$ alkyl,
$R^8$ is selected from hydrogen and $C_1$-$C_6$ alkyl.

Within the frame of the present invention, the expression "neurodegenerative disease or condition" means any disease or condition in which neurodegeneration occurs. Such disease or condition includes, but is not limited to, any disease or condition selected from Alzheimer's disease, Parkinson's disease, amyotrophic lateral sclerosis (ALS), schizophrenia, Huntington's Disease, brain injuries, such as stroke and ischemia, multiple sclerosis, epilepsy, Friedreich's Ataxia, spongiform encephalopaties, amyloidosis, vascular dementia, tauophaties, progressive supranuclear palsy, frontotemporal lobular degeneration, subacute sclerosing panencephalitic parkinsonism, postencephalitic parkinsonism, pugilistic encephalitis, guam parkinsonism-dementia complex, Pick's disease, corticobasal degeneration, frontotemporal dementia, AIDS associated dementia, multiple sclerosis, mood disorders such as depression, schizophrenia and bipolar disorders, promotion of functional recovery post stroke and brain injury, especially traumatic brain injury. In a preferred aspect of the invention, the neurodegenerative disease or condition is Alzheimer's Disease.

Within the frame of the present invention, the expression "haematological disease or condition" means any disease or condition in which disorders of the blood and blood forming tissues occurs. In a preferred embodiment, the haematological disease or condition is selected from thalassaemia, anaemia, aplastic anaemia, Diamond-Blackfan anemia, sickle cell disease, hematologic disorders which require regular red cell transfusions, myelodysplastic syndrome, iron-induced cardiac dysfunction, iron-induced heart failure, and diabetes, more preferably from thalassaemia, anaemia, aplastic anaemia, myelodysplastic syndrome and diabetes.

In a particular aspect, the compound of formula (I) used in the present invention is selected form the following compounds:

4-Methoxy-[1,10]phenanthroline-2-carbaldehyde oxime
4-Chloro-[1,10]phenanthroline-2-carbaldehyde oxime
4-Chloro-[1,10]phenanthroline-2-carbaldehyde
4-Methylsulfanyl-[1,10]phenanthroline-2-carbaldehyde oxime
4-Propylsulfanyl-[1,10]phenanthroline-2-carbaldehyde oxime
4-Ethoxy-[1,10]phenanthroline-2-carbaldehyde oxime
4-Isopropylsulfanyl-[1,10]phenanthroline-2-carbaldehyde oxime
4-(2-Methoxy-ethoxy)-[1,10]phenanthroline-2-carbaldehyde oxime
4-(2-Amino-ethoxy)-[1,10]phenanthroline-2-carbaldehyde oxime
4-(2-Diethylamino-ethoxy)-[1,10]phenanthroline-2-carbaldehyde oxime
4-(2-Methoxy-ethylsulfanyl)-[1,10]phenanthroline-2-carbaldehyde oxime
2-[2-(Hydroxyimino-methyl)-[1,10]phenanthrolin-4-ylsulfanyl]-N,N-dimethyl-acetamide
4-(2,2,2-Trifluoro-ethylsulfanyl)-[1,10]phenanthroline-2-carbaldehyde oxime
[2-(Hydroxyimino-methyl)-[1,10]phenanthrolin-4-ylsulfanyl]-acetic acid methyl ester
4-(Thiazol-2-ylsulfanyl)-[1,10]phenanthroline-2-carbaldehyde oxime
[2-(Hydroxyimino-methyl)-[1,10]phenanthrolin-4-ylsulfanyl]-acetic acid
4-(5-Methyl-thiazol-2-ylsulfanyl)-[1,10]phenanthroline-2-carbaldehyde oxime
4-(5-Methyl-[1,3,4]thiadiazol-2-ylsulfanyl)-[1,10]phenanthroline-2-carbaldehyde oxime
4-([1,3,4]Thiadiazol-2-ylsulfanyl)-[1,10]phenanthroline-2-carbaldehyde oxime
4-Methylsulfanyl-[1,10]phenanthroline-2-carbaldehyde
4-Propylsulfanyl-[1,10]phenanthroline-2-carbaldehyde
4-Propylsulfanyl-[1,10]phenanthroline-2-carbaldehyde oxime
4-Ethoxy-[1,10]phenanthroline-2-carbaldehyde
4-Isopropylsulfanyl-[1,10]phenanthroline-2-carbaldehyde
4-(2-Methoxy-ethoxy)-[1,10]phenanthroline-2-carbaldehyde
4-(2-Diethylamino-ethoxy)-[1,10]phenanthroline-2-carbaldehyde or its salts, solvates or stereoisomers or tautomers thereof.

The compounds used in the present invention may be used with at least other drug to provide a combination therapy. The at least other drug may form part of the same composition, or be provided as a separate composition for administration at the same time or at different time.

According to a further aspect, the present invention is directed to a method of treating or preventing a neurodegenerative or haematological disease or condition, said method comprises administering to a patient in need of such a treatment a therapeutically effective amount of at least one compound of formula (I), its salts or solvates, stereoisomers or tautomers thereof, as defined above or a pharmaceutical composition thereof.

The term "treatment" or "to treat" in the context of this specification means administration of a compound or formulation according to the invention to prevent, ameliorate or eliminate the disease or one or more symptoms associated with said disease. "Treatment" also encompasses preventing, ameliorating or eliminating the physiological sequelae of the disease.

The term "ameliorate" in the context of this invention is understood as meaning any improvement on the situation of the patient treated—either subjectively (feeling of or on the patient) or objectively (measured parameters).

Compounds of Formula I

An embodiment of the invention is directed to a compound of formula (I) wherein $R^1$ is selected from —S—$R^3$, —O—$R^4$ and halogen;

$R^7$ is selected from —CH=N—$OR^8$ or —CHO;

$R^3$ and $R^4$ are independently a $C_1$-$C_6$ alkyl, optionally substituted by $C_1$-$C_6$ alkoxy and/or —$NR^5R^6$, $R^5$ and $R^6$ being independently selected from hydrogen and $C_1$-$C_6$ alkyl, $R^8$ is selected from hydrogen and $C_1$-$C_6$ alkyl;

or any salt or solvate or stereoisomer thereof, with the proviso that when $R^1$ is Cl or $OCH_3$, then $R^7$ is not —CHO or —CH=N—OH.

Preferred compounds are those wherein $R^7$ is —CH=N—$OR^8$, wherein $R^8$ is selected from hydrogen and $C_1$-$C_6$ alkyl. More preferably $R^8$ is hydrogen.

Other preferred compounds are those wherein $R^1$ is —S—$R^3$, wherein $R^3$ is $C_1$-$C_6$ alkyl, optionally substituted by $C_1$-$C_6$ alkyl and/or $NR^5R^6$, being $R^5$ and $R^6$ independently selected from hydrogen and $C_1$-$C_6$ alkyl. Even more preferred compounds are those wherein $R^3$ is selected from methyl, ethyl, propyl and isopropyl.

In another preferred embodiment, $R^1$ is —O—$R^4$, wherein $R^4$ is $C_1$-$C_6$ alkyl, optionally substituted by $C_1$-$C_6$ alkyl and/or $NR^5R^6$, being $R^5$ and $R^6$ independently selected from hydrogen and $C_1$-$C_6$ alkyl. Preferably, $R^4$ is selected from methyl and ethyl. Even more preferably, $R^4$ is ethyl substituted by —$NR^5R^6$ or methoxy, being $R^5$ and $R^6$ independently selected from hydrogen and $C_1$-$C_6$ alkyl. Within this preferred embodiment the amine —$NR^5R^6$ is primary or tertiary, being more preferably diethylamine.

In a further preferred embodiment, the double bond of the oxime group —CH=$NOR^8$ presents E-conformation as shown below:

[Structure: 4-R¹-[1,10]phenanthroline-2-carbaldehyde oxime with =N-OR⁸]

According to a further embodiment, R¹ is chloro.

According to a further embodiment, R¹ is —S-heteroaryl, wherein the heteroaryl group is optionally substituted by $C_1$-$C_6$ alkyl, preferably $C_1$-$C_3$ alkyl, $C_6$-$C_{15}$ aryl, halogen, —(C=O)NR⁵R⁶, —(C=O)OR⁵, $C_1$-$C_6$ alkoxy and/or —NR⁵R⁶.

According to a further embodiment, R³ is a $C_1$-$C_3$ alkyl group substituted by —(C=O)NR⁵R⁶ or —(C=O)OR⁵.

According to a preferred embodiment, the compound of formula (I) is selected from the following compounds:
4-Methoxy-[1,10]phenanthroline-2-carbaldehyde oxime
4-Methylsulfanyl-[1,10]phenanthroline-2-carbaldehyde oxime
4-Propylsulfanyl-[1,10]phenanthroline-2-carbaldehyde oxime
4-Ethoxy-[1,10]phenanthroline-2-carbaldehyde oxime
4-Isopropylsulfanyl-[1,10]phenanthroline-2-carbaldehyde oxime
4-(2-Methoxy-ethoxy)-[1,10]phenanthroline-2-carbaldehyde oxime
4-(2-Amino-ethoxy)-[1,10]phenanthroline-2-carbaldehyde oxime
4-(2-Diethylamino-ethoxy)-[1,10]phenanthroline-2-carbaldehyde oxime
4-(2-Methoxy-ethylsulfanyl)-[1,10]phenanthroline-2-carbaldehyde oxime
2-[2-(Hydroxyimino-methyl)-[1,10]phenanthrolin-4-ylsulfanyl]-N,N-dimethyl-acetamide
4-(2,2,2-Trifluoro-ethylsulfanyl)-[1,10]phenanthroline-2-carbaldehyde oxime
2-[2-(Hydroxyimino-methyl)-[1,10]phenanthrolin-4-ylsulfanyl]acetic acid methyl ester
4-(Thiazol-2-ylsulfanyl)-[1,10]phenanthroline-2-carbaldehyde oxime
[2-(Hydroxyimino-methyl)-[1,10]phenanthrolin-4-ylsulfanyl]-acetic acid
4-(5-Methyl-thiazol-2-ylsulfanyl)-[1,10]phenanthroline-2-carbaldehyde oxime
4-(5-Methyl-[1,3,4]thiadiazol-2-ylsulfanyl)-[1,10]phenanthroline-2-carbaldehyde oxime
4-([1,3,4]Thiadiazol-2-ylsulfanyl)-[1,10]phenanthroline-2-carbaldehyde oxime
4-Methylsulfanyl-[1,10]phenanthroline-2-carbaldehyde
4-Propylsulfanyl-[1,10]phenanthroline-2-carbaldehyde
4-Propylsulfanyl-[1,10]phenanthroline-2-carbaldehyde oxime
4-Ethoxy-[1,10]phenanthroline-2-carbaldehyde
4-Isopropylsulfanyl-[1,10]phenanthroline-2-carbaldehyde
4-(2-Methoxy-ethoxy)-[1,10]phenanthroline-2-carbaldehyde
4-(2-Diethylamino-ethoxy)-[1,10]phenanthroline-2-carbaldehyde
and salts or solvates or stereoisomers or tautomers thereof.

The compounds of formula (I) may be in the form of salts, preferably pharmaceutically acceptable salts, or in the form of solvates. The term "pharmaceutically acceptable salts" refers to any salt which upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. Preferably, "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "solvate" according to this invention is to be understood as meaning any form of the active compound according to the invention which has another molecule (most likely a polar solvent) attached to it via non-covalent bonding. Examples of solvates include hydrates and alcoholates, e.g. methanolate. Preferably, the solvates are pharmaceutically acceptable solvates.

The preparation of salts and solvates can be carried out by methods known in the art. For instance, pharmaceutically acceptable salts of compounds provided herein are synthesized from the parent compound, which contains a basic moiety, by conventional chemical methods. Generally, such salts are, for example, prepared by reacting the free base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate.

One preferred pharmaceutically acceptable form is the crystalline form, including such form in a pharmaceutical composition. In the case of salts and solvates the additional ionic and solvent moieties must also be non-toxic. The compounds of the invention may present different polymorphic forms, it is intended that the invention encompasses all such forms.

The compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon or a nitrogen by $^{15}$N-enriched nitrogen are within the scope of this invention.

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

Pharmaceutical Compositions

According to a further aspect, the present invention is directed to a pharmaceutical composition comprising at least one compound of formula (I) as defined above, its salts or solvates or stereoisomers or tautomers thereof, and at least one pharmaceutically acceptable carrier.

The term "carrier" refers to a diluent, adjuvant, excipient, or vehicle with which the active ingredient is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 1995.

Preferably, the carriers of the invention are approved by a regulatory agency of the Federal or a state government or listed in the U.S. Pharmacopeia or other generally recognized pharmacopeia for use in animals, and more particularly in humans The carriers and auxiliary substances necessary to manufacture the desired pharmaceutical form of administration of the pharmaceutical composition of the invention will depend, among other factors, on the elected administration pharmaceutical form. Said pharmaceutical forms of administration of the pharmaceutical composition will be manufactured according to conventional methods known by the skilled person in the art. A review of different active ingredient administration methods, excipients to be used and processes for producing them can be found in "Tratado de Farmacia Galénica", C. Faulí i Trillo, Luzán 5, S. A. de Ediciones, 1993.

Examples of pharmaceutical compositions include any solid (tablets, pills, capsules, granules etc.) or liquid (solutions, suspensions or emulsions) compositions for oral, topical or parenteral administration.

In a preferred embodiment the pharmaceutical compositions are in oral form. Suitable dose forms for oral administration may be tablets and capsules and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycolate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

The compounds or compositions of the present invention may be administered by any suitable method, such as intravenous infusion, oral preparations, and intraperitoneal and intravenous administration. Oral administration is preferred because of the convenience for the patient and the chronic character of many of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.01 to 1000 mg/kg/day.

According to a further aspect, the present invention is directed to a compound of formula (I), its salts or solvates or stereoisomers or tautomers thereof, as defined above, for use as a medicament.

Process for the Synthesis of a Compound of Formula I

The compounds of the present invention may be prepared by a combination of reactions known in the art.

In a particular embodiment, the compounds of formula (I) can be prepared by a process comprising:

a) oxidizing the methyl group of the compound of formula (II) with an oxidizing agent to form a compound of formula (I):

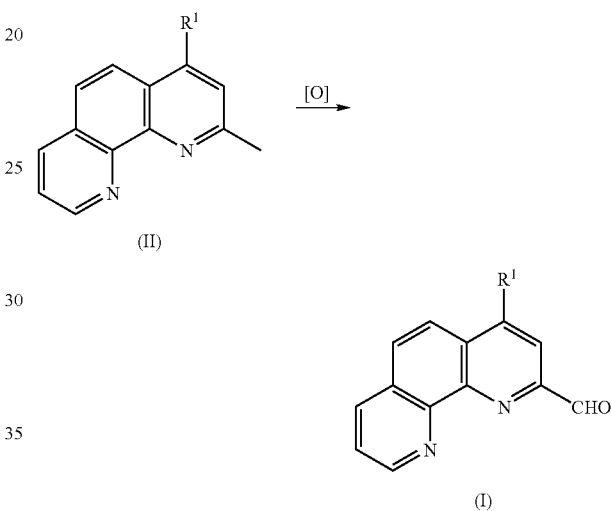

wherein $R^1$ is selected from $-SR^3$, $-OR^4$ and halogen, being $R^3$ and $R^4$ independently selected from the group consisting of $C_1$-$C_6$ alkyl, $C_6$-$C_{15}$ aryl and heteroaryl, optionally substituted by $C_1$-$C_6$ alkyl, $C_6$-$C_{15}$ aryl, halogen, $-(C=O)NR^5R^6$, $-(C=O)OR^5$, $C_1$-$C_6$ alkoxy and/or $-NR^5R^6$; and wherein $R^5$ and $R^6$ are independently selected form hydrogen and $C_1$-$C_6$-alkyl, and optionally, b) converting the aldehyde group $-CHO$ in the compound of formula (I) into an oxime group $-CH=N-OR^8$, being $R^8$ selected from hydrogen and $C_1$-$C_6$ alkyl, in the presence of hydroxylamine or $O-(C_1$-$C_6)$alkylhydroxylamine:

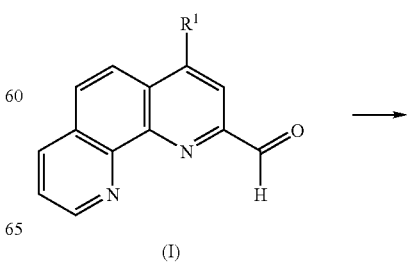

-continued

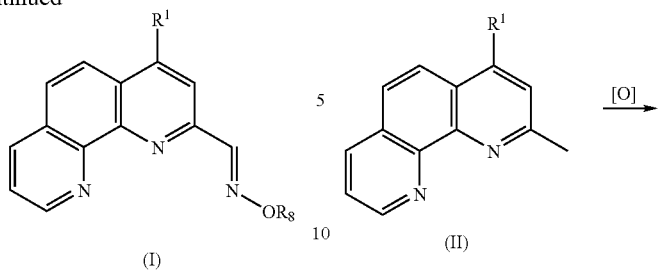

(I)

According to a preferred embodiment the oxidation in step a) is carried out in the presence of oxidising agents well known to the person skilled in the art. The election of the most suitable reagent is a matter of routine experimentation for said person skilled. However, according to a preferred embodiment, the oxidation reaction is carried out in the presence of $SeO_2$. The solvent used in said step a) can be, but is not limited to, dioxane.

According to another preferred embodiment the step b) can be carried out in a mixture of an alcohol, such as ethanol, and an aqueous sodium salt, such as sodium hydroxide.

In a further aspect, the present invention refers to a process for the preparation of a compound of formula (I) which comprises:

a) reacting the compound formula (III) with a sodium salt of the corresponding alcoxide or thiolate of formula —$OR^3$ or —$OR^4$, to form a compound of formula (II):

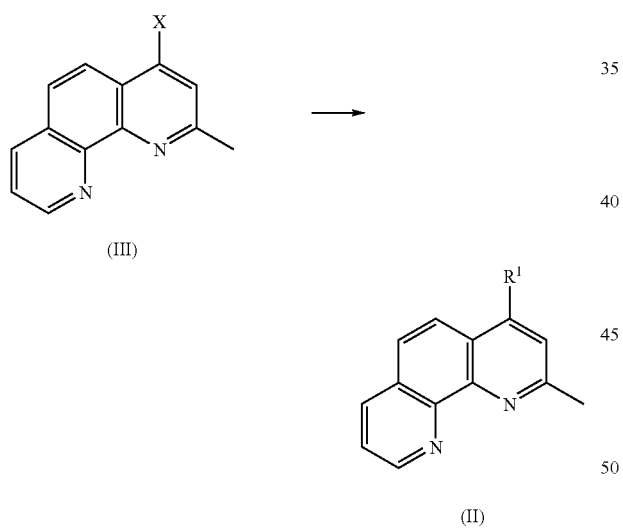

wherein
X is an halogen;
$R^1$ is selected from —S—$R^3$, —O—$R^4$ and halogen;
$R^3$ and $R^4$ are independently selected from the group consisting of $C_1$-$C_6$ alkyl, $C_6$-$C_{15}$ aryl and heteroaryl, optionally substituted by $C_1$-$C_6$ alkyl, $C_6$-$C_{15}$ aryl, halogen, —(C=O)$NR^5R^6$, —(C=O)$OR^5$, $C_1$-$C_6$ alkoxy and/or —$NR^5R^6$;
provided that when $R^1$ in the formula (II) is an halogen this step is omitted;
b) oxidising the methyl group of the compound of formula (II) with an oxidizing agent to form a compound of formula (I);

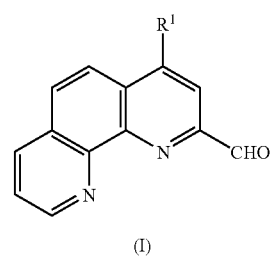

(I)

wherein $R^1$ is as defined in step a);
and, optionally
c) converting the aldehyde group —CHO in the compound of formula (I) into an oxime group —CH=N—$OR^8$, being $R^8$ selected from hydrogen and $C_1$-$C_6$ alkyl, in the presence of hydroxylamine or O—($C_1$-$C_6$)alkylhydroxylamine:

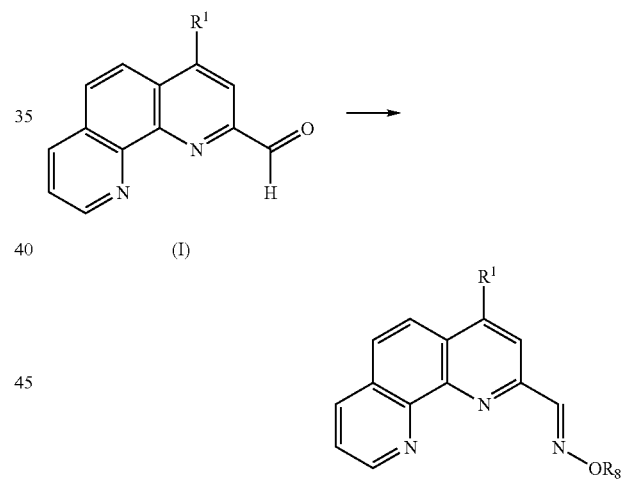

wherein $R^1$ is as defined in step a).

The corresponding alkoxide or thiolate as defined is step a) results from the reaction of the corresponding alcohol or thiol with a suitable inorganic sodium salt. In a preferred embodiment, the sodium salt is sodium ethoxide, sodium 2-propanethiolate or sodium 1-propanethiolate.

In another preferred embodiment of this process, step a) is carried out in an alcohol or tetrahydrofurane as solvent.

The starting compound of formula (III) can be prepared by methods known by a skilled person. For example, it may be synthesized by first reacting the compound quinolin-8-ylamine with ethyl acetoacetate in the presence of hydrochloride acid as catalyst to form 2-methyl-[1,10]phenanthrolin-4- ol, according to the process described in *Proc. R. Soc. N. S. W.* 1938, 71, 462-474. Subsequently, the phenanthroline obtained in the first reaction is subjected to an halogenation reaction, such as for example in the presence of POCl₃, to form the compound of formula (III), according to the process described in *J. Med. Chem.*, 2003, 46, 4463-4476.

In the following, the present invention is further illustrated by examples. They should in no case be interpreted as a limitation of the scope of the invention as defined in the claims.

EXAMPLES

In the present examples, the following compounds of formula (I) are being referred to:

Compound 1
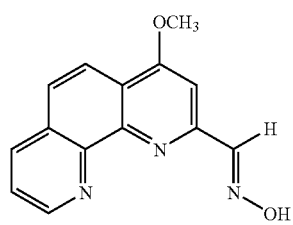

Compound 2
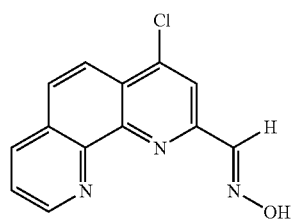

Compound 3
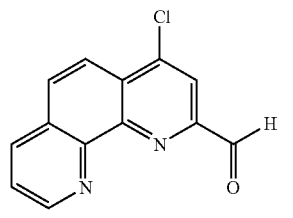

Compound 4
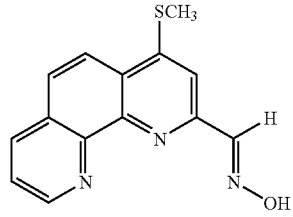

Compound 5
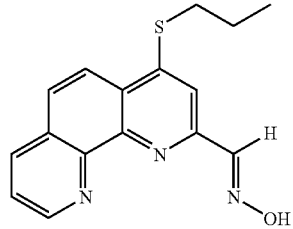

Compound 6
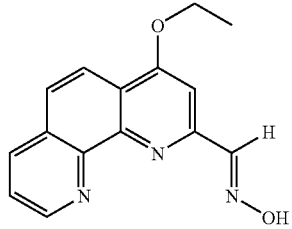

Compound 7
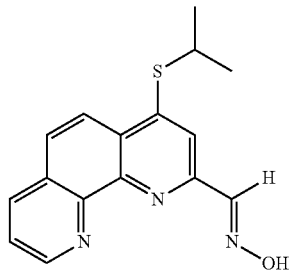

Compound 8
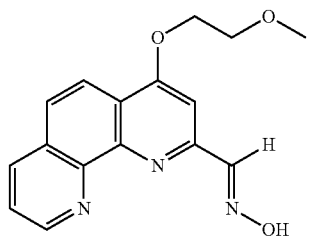

Compound 9
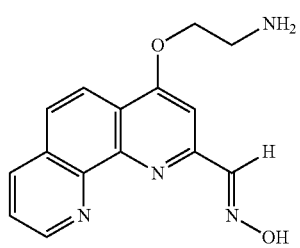

Compound 10
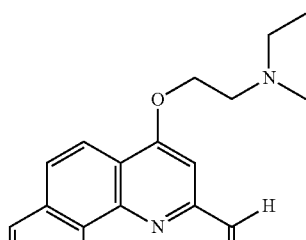

Compound 12
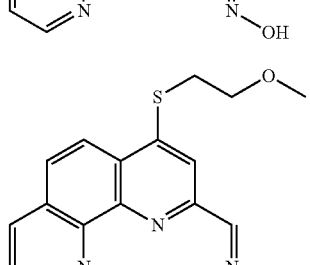

Compound 13

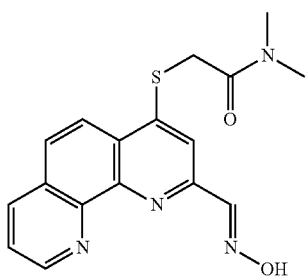

Compound 14

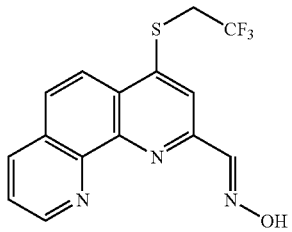

Compound 15

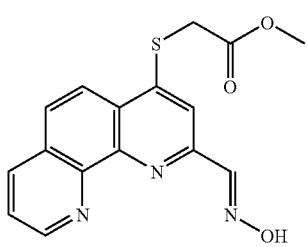

Compound 16

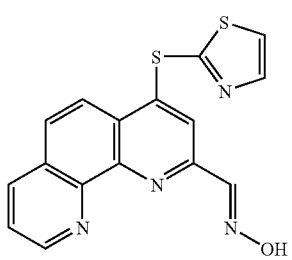

Compound 17

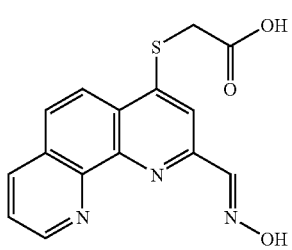

Compound 18

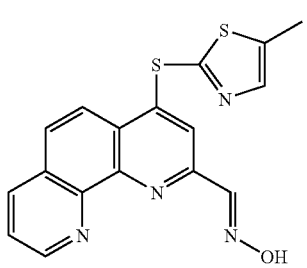

Compound 19

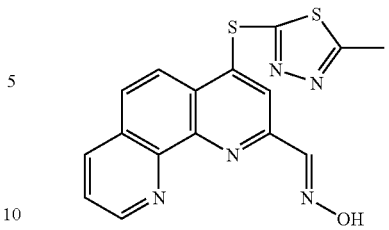

Compound 20

Synthesis of the Compounds

Compounds of formula (I) according to the present invention were prepared following the general preparation strategy detailed below.

In the following, the particular syntheses of compounds 4 to 10, with structures as detailed in table 1, are described.

The compounds 4 to 10 were synthesized starting from a common intermediate for which the method of preparation is described below.

Synthesis of the Intermediate
4-chloro-2-methyl-[1,10]phenanthroline

1. Preparation of 2-Methyl-[1,10]phenathrolin-4-ol

Synthetic procedure was adapted from Hazlewood, S. J.; Hughes, G. K.; Lions F., *J. Proc. R. Soc. N. S. W.* 1938, 71, 462-474.

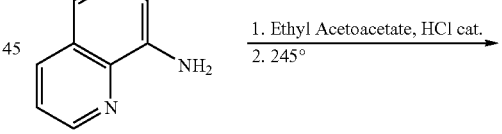

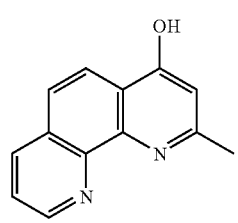

In a 100 mL round-bottomed flask 8-aminoquinoline (15.00 g, 104.0 mmol) and ethyl acetoacetate (13.50 g, 104.0 mmol) were stirred at 100° C. for 24 hours in the presence of a catalytic amount of 1N HCl (10 drops). The reaction mixture was allowed to reach room temperature and toluene (20 mL) was added, which was later removed in a rotary evaporator. The same process of dilution with toluene and solvent removal was repeated at least three times. The dark oily crude enamine obtained was dissolved in diphenyl ether (20 mL) and was transferred to an addition funnel connected to a 250 mL round-bottomed flask containing diphenyl ether (100 mL). The flask was heated to reflux and the enamine solution was slowly added over a period of 15 minutes, and reflux was mantained for additional 20 minutes. The reaction mixture was cooled down to room temperature and the crystalline material formed was filtered, washed with ethyl ether and dried. A light brown solid (10.20 g, 47% yield) was obtained.

2. Preparation of 4-Chloro-2-methyl-[1,10]phenanthroline

Synthetic procedure was adapted from Harrison R. J.; Cuesta J.; Chessari, G.; Read M. A.; Basra, S. K.; Reszka, A. P.; Morrell, J.; Gowan, S. M.; Incles, C. M.; Tanious, F. A.; Wilson, W. D.; Kelland, L. R.; Neidle, S., *J. Med. Chem.* 2003, 46, 4463-4476.

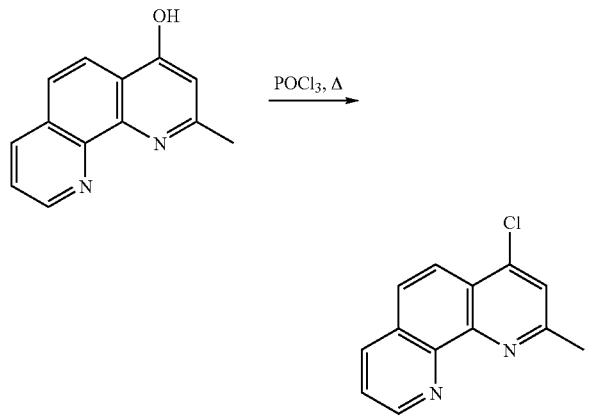

To a 500 mL round-bottomed flask equipped with a reflux condenser containing 2-methyl-[1,10]phenanthrolin-4-ol, (10.20 g, 48.5 mmol), was slowly added phosphorus oxychloride (200 mL) and the mixture was refluxed for 3 hours. The reaction flask was allowed to cool down to room temperature and the solvent was removed in a rotary evaporator. The solid obtained was treated with methylene chloride (200 mL) and saturated NaHCO$_3$ (200 mL) and transferred to a separatory funnel. The aqueous layer was further extracted with methylene chloride (200 mL) and the combined organic layers were washed with brine (200 mL), dried (Na$_2$SO$_4$), filtered and concentrated. The residue obtained was treated with ethyl ether (100 mL), filtered and dried yielding a light brown solid (9.00 g). A second crop of 0.60 g of material was obtained from the mother liquors as a light yellow solid, with an overall yield of 9.60 g (87% yield).

Example 1

Preparation of 4-Methylsulfanyl -[1,10]phenanthroline-2-carbaldehyde oxime (Compound 4)

1. Synthesis of 2-Methyl-4-methylsulfanyl-[1,10]phenanthroline

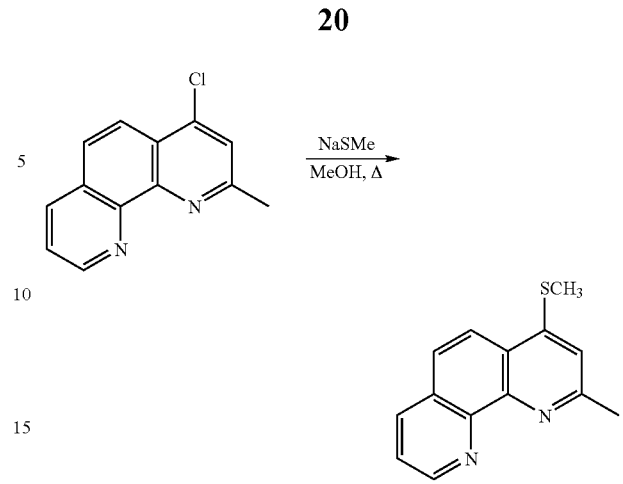

Solid sodium methanethiolate (3.30 g, 47.7 mmol) was added to a 100 mL round-bottomed flask containing a solution of 4-chloro-2-methyl-[1,10]phenanthroline (intermediate obtained previously), (2.10 g, 9.4 mmol) in methanol (50 mL). The reaction mixture was refluxed for 18 hours and allowed to cool down to room temperature afterwards. The solvent was removed in a rotary evaporator and the residue was treated with methylene choride (100 mL) and saturated NaHCO$_3$ (100 mL) and transferred to a separatory funnel. The organic layer was washed with brine (100 mL), dried (Na$_2$SO$_4$), filtered and concentrated in vacuo. The solid residue was treated with ethyl ether, filtered and dried, yielding 1.90 g of a light brown solid (84%).

2. Synthesis of 4-Methylsulfanyl-[1,10]phenanthroline-2-carbaldehyde

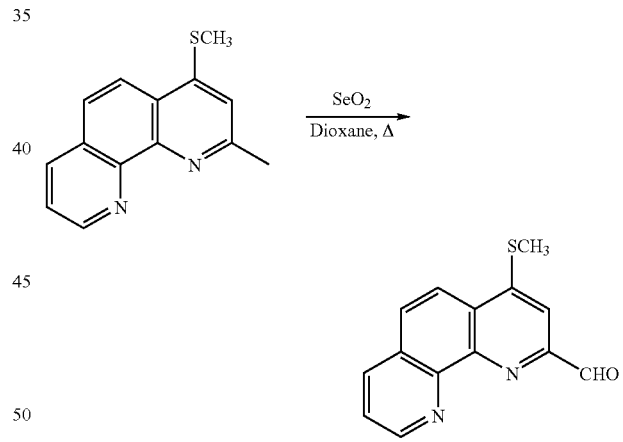

A solution of SeO$_2$ (2.18 g, 19.6 mmol) in a mixture of dioxane (100 mL) and water (4 mL) was heated to reflux in a two-neck 250 mL round-bottomed flask. A solution of 2-methyl-4-methylsulfanyl-[1,10]phenanthroline (1.89 g, 7.90 mmol) in hot dioxane (100 mL) was added through an addition funnel over a period of 1 hour and the reaction mixture was refluxed for additional 45 minutes. The reaction mixture was filtered while hot and the residue rinsed with more hot dioxane (20 mL) and filtered. The filtrate was concentrated in vacuo and the residue obtained was redissolved in hot water, stirred with decolorizing charcoal and filtered. The filtrate was allowed to reach room temperature and basified with saturated NaHCO$_3$ until precipitation of a white solid, which was filtered, washed with cold water and dried in vacuo. A white solid (0.80 g, 41% yield) was obtained.

3. Synthesis of 4-Methylsulfanyl-[1,10]phenanthroline-2-carbaldehyde oxime

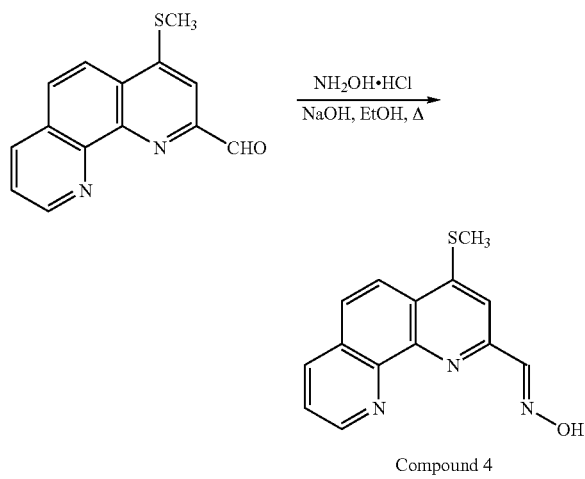

Compound 4

To a 25 mL round-bottomed flask containing a solution of 4-methylsulfanyl-[1,10]phenanthroline-2-carbaldehyde (228.0 mg, 1.1 mmol) in ethanol (3.2 mL), a solution of hydroxylamine hydrochloride (707.0 mg, 10.2 mmol) in water (5.0 mL) was added followed by the addition of 10% NaOH until a precipitate was formed. The reaction mixture was heated to 90° for about 30 minutes, cooled to room temperature and the white precipitate was filtered, washed with cold water and dried. White solid (240.0 mg, 100%) was obtained.

$^1$H-NMR (DMSO-$d_6$, 400 MHz):

11.95 (s, 1H); 9.12 (dd, 1H, J=1.6, 4.2 Hz); 8.50 (dd, 1H, J=1.6, 8.1 Hz); 8.33 (s, 1H); 8.06 (AB system, 2H, $S_{AB}$=9.1 Hz); 7.92 (s, 1H); 7.78 (dd, 1H, J=4.2, 8.1 Hz); 2.72 (s, 3H)

$^{13}$C NMR (DMSO-$d_6$, 100 MHz):

151.2; 150.3; 149.1; 148.5; 145.1; 144.2; 136.2; 128.4; 127.1; 125.3; 123.5; 121.1; 121.0; 112.5; 13.4

Example 2

Synthesis of 4-Propylsulfanyl-[1,10]phenanthroline-2-carbaldehyde oxime (Compound 5).

1. Synthesis of 2-Methyl-4-propylsulfanyl-[1,10]phenanthroline

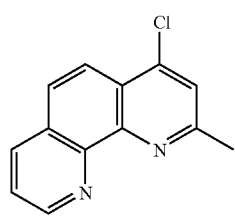

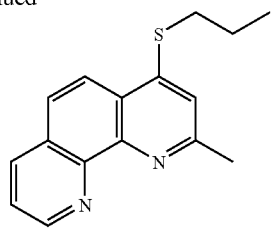

Solid sodium 1-propanethiolate (2.35 g, 24.0 mmol) was added to a 100 mL round-bottomed flask containing a solution of 4-chloro-2-methyl-[1,10]phenanthroline (1.10 g, 4.8 mmol) in methanol (50 mL). The reaction mixture was refluxed for 18 hours and allowed to reach room temperature. The solvent was removed in a rotary evaporator and the residue was treated with methylene choride (100 mL) and saturated NaHCO$_3$ (100 mL) and transferred to a separatory funnel. The organic layer was washed with brine (100 mL), dried (Na$_2$SO$_4$), filtered and concentrated in vacuo. The solid residue was treated with ethyl ether, filtered, and dried yielding 0.98 g of a dark orange solid (76%).

2. Synthesis of 4-Propylsulfanyl-[1,10]phenanthroline-2-carbaldehyde

A solution of SeO$_2$ (0.98 g, 8.8 mmol) in a mixture of dioxane (50 mL) and water (2 mL) was heated to reflux in a two-neck 250 mL round-bottomed flask. A solution of 2-methyl-4-propylsulfanyl-[1,10]phenanthroline (0.95 g, 3.5 mmol) in hot dioxane (50 mL) was added through an addition funnel over a period of 30 minutes and the reaction mixture was refluxed for additional 1 hour. The reaction mixture was filtered while hot and the residue rinsed with more hot dioxane (20 mL) and filtered. The filtrates were combined and evaporated in vacuo and the residue was treated with methylene chloride (100 mL) and a 10% K$_2$CO$_3$ aqueous solution (100 mL). The aqueous layer was extracted several times with methylene chloride (3×100 mL) and the combined organic layers were washed with brine, dried (Na$_2$SO$_4$), filtered and concentrated. The crude product was purified by flash chromatography (neutral Al$_2$O$_3$, MeOH/DCM, 1:50 to 1:15) to afford the pure product as a brown solid (0.27 g, 27%).

3. Synthesis of 4-Propylsulfanyl-[1,10]phenanthroline-2-carbaldehyde oxime

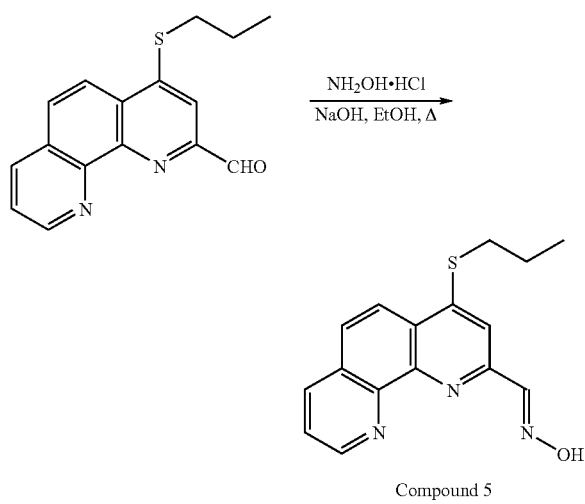

Compound 5

The final step to obtain the Compound 5 is carried out in the same way as described in the synthesis of Compound 4.

$^1$H-NMR (DMSO-d$_6$, 400 MHz):
11.96 (s, 1H); 9.11 (dd, 1H, J=1.6, 4.0 Hz); 8.49 (dd, 1H, J=1.6, 8.0 Hz); 8.33 (s, 1H); 8.10 (d, 1H, J=9.2 Hz); 8.03 (d, 1H, J=9.2 Hz); 7.96 (s, 1H); 7.78 (dd, 1H, J=4.0, 8.0 Hz); 3.23 (t, 2H, J=7.2 Hz); 1.79 (m, 2H); 1.08 (t, 3H, J=7.2 Hz)

$^{13}$C NMR (DMSO-d$_6$, 100 MHz):
151.09; 150.29; 149.14; 147.45; 145.17; 144.54; 136.20; 128.42; 127.09; 125.59; 123.50; 121.25; 113.31; 32.19; 21.00; 13.28

Example 3

Preparation of 4-Ethoxy-[1,10]phenanthroline-2-carbaldehyde oxime (Compound 6)

1. Synthesis of 2-Methyl-4-ethoxy-[1,10]phenanthroline

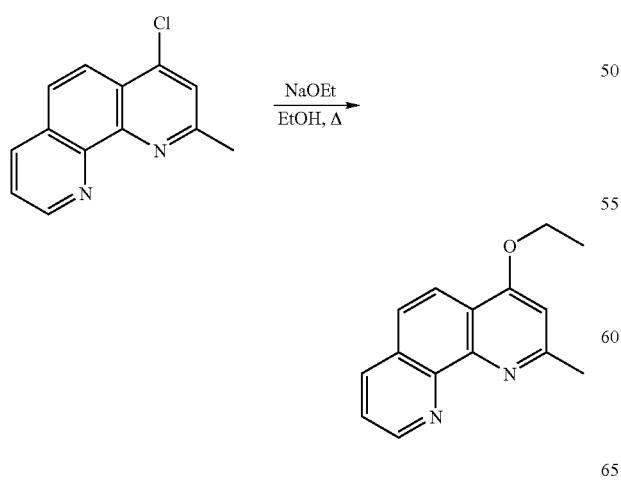

Solid sodium ethoxide (2.97 g, 48.0 mmol) was added to a 100 mL round-bottomed flask containing a solution of 4-chloro-2-methyl-[1,10]phenanthroline (1.10 g, 4.8 mmol) in ethanol (50 mL). The reaction mixture was refluxed for 18 hours. The solvent was removed in a rotary evaporator and the residue was treated with methylene choride (100 mL) and saturated NaHCO$_3$ (100 mL) and transferred to a separatory funnel. The organic layer was washed with brine (100 mL), dried (Na$_2$SO$_4$), filtered and concentrated in vacuo. The solid residue was treated with ethyl ether, filtered, and dried yielding 0.89 g of a brown solid (78%).

2. Synthesis of 4-Ethoxy-[1,10]phenanthroline-2-carbaldehyde

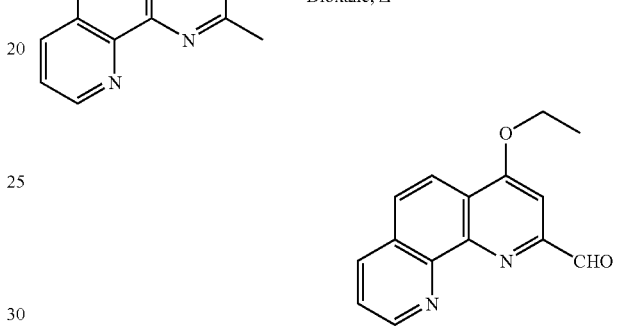

A solution of SeO$_2$ (1.01 g, 9.1 mmol) in a mixture of dioxane (50 mL) and water (2 mL) was heated to reflux in a two-neck 250 mL round-bottomed flask. A solution of 2-methyl-4-ethoxy-[1,10]phenanthroline (0.87 g, 3.6 mmol) in hot dioxane (50 mL) was added through an addition funnel over a period of 30 minutes and the reaction mixture was refluxed for 1 hour. The reaction mixture was filtered while hot and the residue rinsed with more hot dioxane (20 mL) and filtered. The filtrates were combined and concentrated in vacuo and the residue was treated with methylene chloride (100 mL) and a 10% K$_2$CO$_3$ aqueous solution (100 mL). The aqueous layer was extracted with methylene chloride (3×100 mL) and the combined organic layers were washed with brine, dried (Na$_2$SO$_4$), filtered and concentrated. The crude product was purified by flash chromatography (SiO$_2$, MeOH/DCM, 1:30 to 1:15) to afford the pure product as a light brown solid (0.15 g, 16%).

3. Synthesis of 4-Ethoxy-[1,10]phenanthroline-2-carbaldehyde oxime

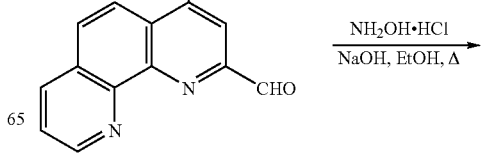

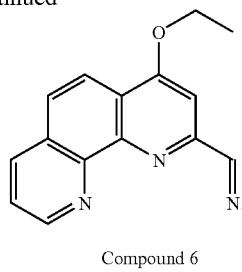

Compound 6

The final step to obtain the Compound 6 is carried out in the same way as described in the synthesis of Compound 4.

$^1$H NMR (DMSO-$d_6$, 400 MHz):

11.85 (s, 1H); 9.10 (dd, 1H, J=1.6, 4.0 Hz); 8.48 (dd, 1H, J=1.6, 8.0 Hz); 8.32 (s, 1H); 8.17 (d, 1H, J=9.2 Hz); 7.96 (d, 1H, J=9.2 Hz); 7.76 (dd, 1H, J=4.0, 8.0 Hz); 7.57 (s, 1H); 4.39 (q, 2H, J=6.8 Hz); 1.52 (t, 3H, J=6.8 Hz)

$^{13}$C NMR (DMSO-$d_6$, 100 MHz):

160.85; 153.28; 149.96; 149.61; 146.06; 144.96; 136.15; 128.61; 126.05; 123.27; 120.27; 119.57; 99.11; 64.34; 14.22

Example 4

Preparation of 4-Isopropylsulfanyl-[1,10]phenanthroline-2-carbaldehyde oxime (Compound 7).

1. Synthesis of 2-Methyl-4-isopropylsulfanyl-[1,10]phenanthroline

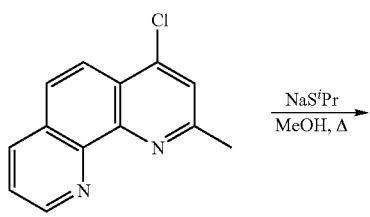

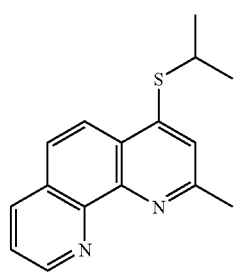

Solid sodium 2-propanethiolate (2.35 g, 24.0 mmol) was added to a 100 mL round-bottomed flask containing a solution of 4-chloro-2-methyl-[1,10]phenanthroline (1.10 g, 4.8 mmol) in methanol (50 mL). The reaction mixture was refluxed for 18 hours. The solvent was removed in a rotary evaporator and the residue was treated with methylene choride (100 mL) and saturated NaHCO$_3$ (100 mL) and transferred to a separatory funnel. The organic layer was washed with brine (100 mL), dried (Na$_2$SO$_4$), filtered and concentrated in vacuo. The residue was purified by flash chromatography (SiO$_2$, MeOH/DCM, 1:80) to afford the pure product as a yellow oil (1.03 g, 80%).

2. Synthesis of 4-Isopropylsulfanyl-[1,10]phenanthroline-2-carbaldehyde

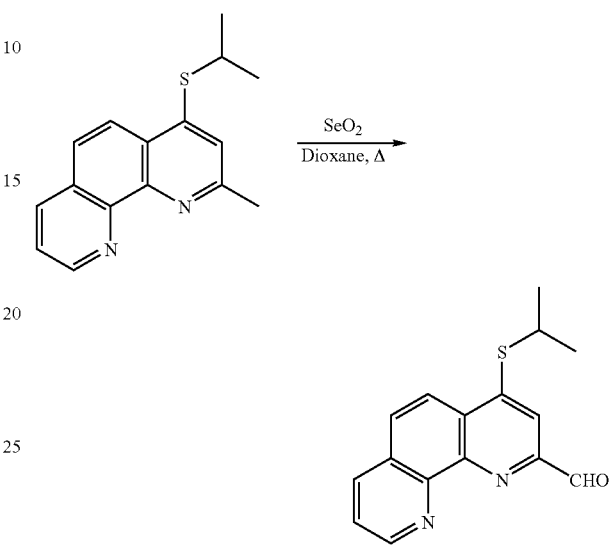

A solution of SeO$_2$ (1.06 g, 9.6 mmol) in a mixture of dioxane (50 mL) and water (2 mL) was heated to reflux in a two-neck 250 mL round-bottomed flask. A solution of 2-methyl-4-isopropylsulfanyl-[1,10]phenanthroline (1.03 g, 3.8 mmol) in hot dioxane (50 mL) was added through an addition funnel over a period of 30 minutes and the reaction mixture was refluxed for 1 hour. The reaction mixture was filtered while hot and the residue rinsed with more hot dioxane (20 mL) and filtered. The filtrates were combined and concentrated in vacuo and the residue was treated with methylene chloride (100 mL) and a 10% K$_2$CO$_3$ aqueous solution (100 mL). The aqueous layer was extracted several times with methylene chloride (3×100 mL) and the combined organic layers were washed with brine, dried (Na$_2$SO$_4$), filtered and concentrated. The crude product was purified by flash chromatography (neutral Al$_2$O$_3$, MeOH/DCM, 1:50 to 1:15) to afford the pure product as a light yellow solid (0.44 g, 41%).

3. Synthesis of 4-Isopropylsulfanyl-[1,10]phenanthroline-2-carbaldehyde oxime

The final step to obtain the Compound 7 is carried out in the same way as described in the synthesis of Compound 4.

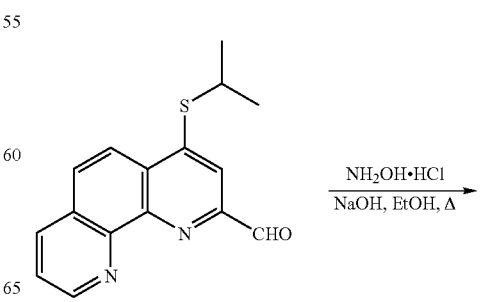

-continued

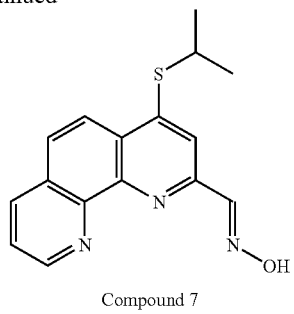

Compound 7

$^1$H NMR (DMSO-d$_6$, 400 MHz):

11.98 (s, 1H); 9.12 (dd, 1H, J=1.6, 4.0 Hz); 8.51 (dd, 1H, J=1.6, 8.0 Hz); 8.35 (s, 1H); 8.12 (d, 1H, J=9.2 Hz); 8.04 (d, 1H, J=9.2 Hz); 8.03 (s, 1H); 7.79 (dd, 1H, J=4.0, 8.0 Hz, 1H); 3.89 (m, 1H); 1.46(d, 6H, J=6.4 Hz)

$^{13}$C NMR (DMSO-d$_6$, 100 MHz):

151.12; 150.28; 149.13; 146.52; 145.18; 144.81; 136.19; 128.43; 127.11; 125.97; 123.52; 121.44; 114.84; 35.40; 22.27

Example 5

Preparation of 4-(2-Methoxy-ethoxy)-[1,10]phenanthroline-2-carbaldehyde oxime (Compound 8).

1. Synthesis of 4-(2-Methoxy-ethoxy)-2-methyl-[1,10]phenanthroline

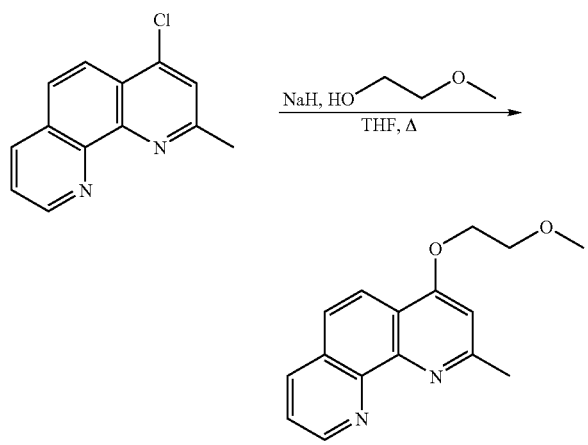

To a suspension of sodium hydride (60% in mineral oil, 1.75 g, 43.7 mmol) in THF (30 mL) a solution of 2-methoxy-ethanol (3.30 g, 43.7 mmol) in anhydrous THF (10 mL) was slowly added. The mixture was stirred at room temperature for 20 minutes and a solution of 4-chloro-2-methyl-[1,10] phenanthroline (2.00 g, 8.8 mmol) in anhydrous THF (20 mL) was added. The reaction mixture was refluxed for 18 hours and the solvent was removed in a rotary evaporator. The residue was treated with methylene choride (100 mL) and saturated NaHCO$_3$ (100 mL) and transferred to a separatory funnel. The organic layer was washed with brine (100 mL), dried (Na$_2$SO$_4$), filtered and concentrated in vacuo. The residue was washed with hexane and purified by flash chromatography (SiO$_2$, MeOH/DCM, 1:30) to afford the pure product as a light yellow solid (1.17 g, 50%).

2. Synthesis of 4-(2-Methoxy-ethoxy)-[1,10]phenanthroline-2-carbaldehyde

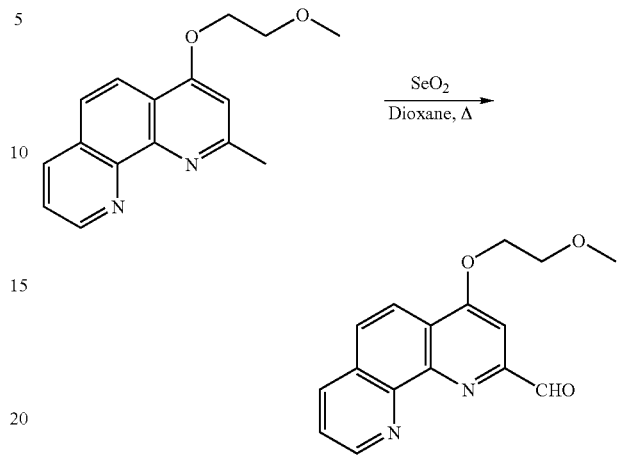

A solution of SeO$_2$ (1.19 g, 10.8 mmol) in a mixture of dioxane (50 mL) and water (2 mL) was heated to reflux in a two-neck 250 mL round-bottomed flask. A solution of 4-(2-methoxy-ethoxy)-2-methyl-[1,10]phenanthroline (1.16 g, 4.3 mmol) in hot dioxane (30 mL) was added through an addition funnel over a period of 10 minutes and the reaction mixture was refluxed for 30 minutes. The solvent was evaporated in vacuo and the residue was treated with methylene chloride (200 mL) and saturated NaHCO$_3$ (200 mL). The aqueous layer was extracted several times with methylene chloride (3×100 mL) and the combined organic layers were washed with brine, dried (Na$_2$SO$_4$), filtered and evaporated. The crude product was purified by flash chromatography (SiO$_2$, MeOH/DCM, 1:40 to 1:20) to afford the pure product as a pale solid (0.65 g, 53%).

3. Synthesis of 4-(2-Methoxy-ethoxy)-[1,10]phenanthroline-2-carbaldehyde oxime

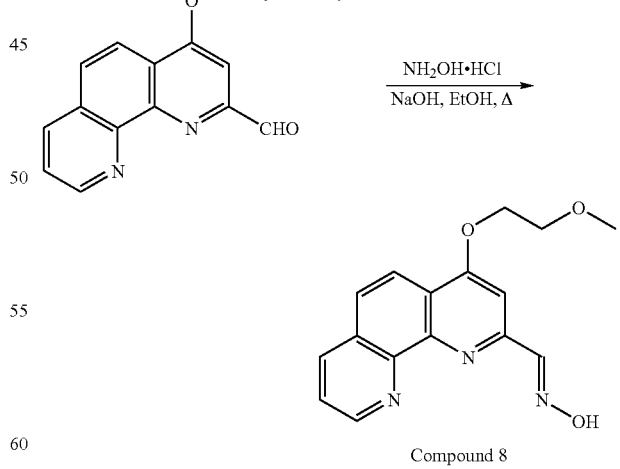

Compound 8

The final step to obtain the Compound 8 is carried out in the same way as described in the synthesis of Compound 4.

$^1$H NMR (DMSO-d$_6$, 400 MHz):

11.94 (s, 1 H); 9.06 (dd, 1 H, J=1.6, 4.0 Hz); 8.46 (dd, 1 H, J=1.2, 8.0 Hz); 8.35 (s, 1 H); 8.13 (d, 1H, J=8.8 Hz); 7.95 (d,

1H, J=8.8 Hz); 7.75 (dd, 1H, J=4.4, 8.0 Hz); 7.57 (s, 1H); 4.43 (t, 2H, J=4.4 Hz); 3.83 (t, 2H, J=4.4 Hz); 3.36 (s, 3H)

$^{13}$C NMR (DMSO-d$_6$, 100 MHz):

161.3; 153.5; 150.3; 150.0; 146.1; 145.0; 136.6; 128.9; 126.4; 123.7; 120.5; 119.9; 99.7; 70.2; 68.4; 58.6

Example 6 preparation of 4-(2-Amino-ethoxy)-[1,10]phenan-throline-2-carbaldehyde oxime (Compound 9).

1. Synthesis of [2-(2-Methyl-[1,10]phenanthrolin-4-yloxy)-ethyl]-carbamic acid tert-butyl ester

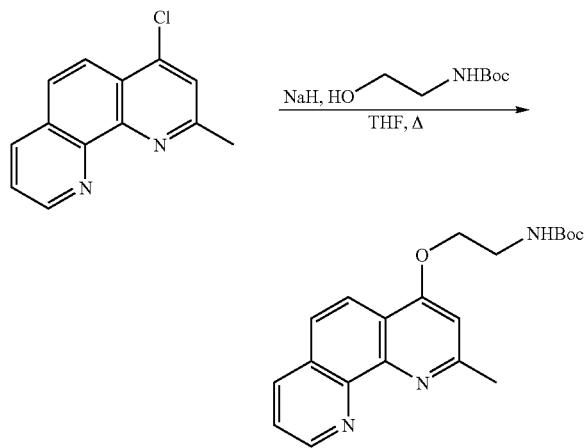

To a suspension of sodium hydride (60% in mineral oil, 0.87 g, 21.8 mmol) in THF (15 mL) a solution of N-Boc-2-hydroxyethylamine (1.75 g, 21.8 mmol) in anhydrous THF (5 mL) was slowly added. The mixture was stirred at room temperature for 20 minutes and a solution of 4-chloro-2-methyl-[1,10]phenanthroline (1.00 g, 4.4 mmol) in anhydrous THF (20 mL) was slowly added. The reaction mixture was refluxed for 18 hours and the solvent was removed in a rotary evaporator. The residue was treated with methylene choride (100 mL) and saturated NaHCO$_3$ (100 mL) and transferred to a separatory funnel. The organic layer was washed with brine (100 mL), dried (Na$_2$SO$_4$), filtered and concentrated in vacuo. The residue was washed with hexane and purified by flash chromatography (SiO$_2$, MeOH/DCM, 1:40) to afford the pure product as a pale solid (0.72 g, 46%).

2. Synthesis of [2-(2-Formyl-[1,10]phenanthrolin-4-yloxy)-ethyl]carbamic acid tert-butyl ester

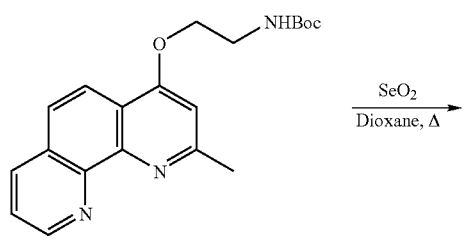

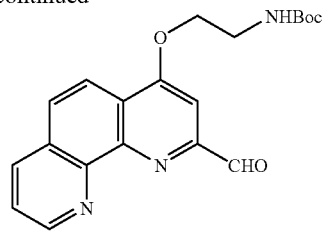

A solution of SeO$_2$ (0.56 g, 5.1 mmol) in a mixture of dioxane (25 mL) and water (2 mL) was heated to reflux in a two-neck 100 mL round-bottomed flask. A solution of [2-(2-methyl-[1,10]phenanthrolin-4-yloxy)-ethyl]carbamic acid tert-butyl ester (0.72 g, 2.0 mmol) in hot dioxane (20 mL) was added through an addition funnel over a period of 15 minutes and the reaction mixture was refluxed for 45 minutes. The solvent was evaporated in vacuo and the residue was treated with methylene chloride (100 mL) and saturated NaHCO$_3$ (100 mL). The aqueous layer was extracted with methylene chloride (3×100 mL) and the combined organic layers were washed with brine, dried (Na$_2$SO$_4$), filtered and concentrated. The crude product was obtained as a yellow solid (0.52 g, 69%) and was pure enough to be used in further synthetic steps without additional purification.

3. Synthesis of 4-(2-Amino-ethoxy)-[1,10]phenanthroline-2-carbaldehyde oxime

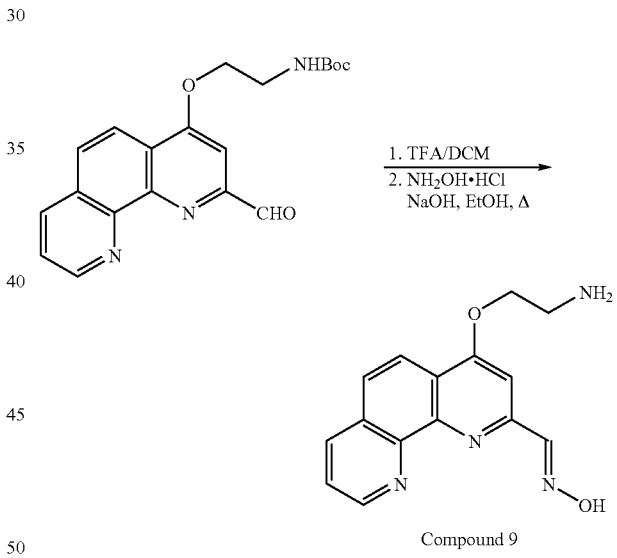

Compound 9

A solution of [2-(2-formyl-[1,10]phenanthrolin-4-yloxy)-ethyl]carbamic acid tert-butyl ester (0.52 g, 1.4 mmol) was stirred for 1 hour at room temperature in a mixture of trifluoroacetic acid (5 mL) and methylene chloride (10 mL). The solvent was removed and the residue was dried and redissolved in ethanol (5 mL). A solution of hydroxylamine hydrochloride (0.88 g, 12.7 mmol) in water (7 mL) was added followed by the addition of 10% NaOH until a white precipitate formed. The mixture was heated to reflux for 1 hour, cooled down to room temperature and the white precipitate filtered, washed with cold water and dried. The title compound was isolated as a pale solid (37.0 mg, 9%)

$^1$H NMR (DMSO-d$_6$, 400 MHz):

12.13 (s, 1H); 9.09 (dd, 1H, J=1.2 Hz, J=4.0 Hz); 8.50 (dd, 1H, J=1.2 Hz, J=8.0 Hz); 8.40 (m, 2H); 7.97 (d, 1H, J=8.8

Hz); 7.81 (dd, 1H, J=4.0 Hz, J=8.0 Hz); 7.26 (s, 1H); 3.73 (d, 2H, J=9.2 Hz); 3.52 (d, 2H, J=9.2 Hz)

$^{13}$C NMR (DMSO-d$_6$, 100 MHz):

152.72, 150.00, 146.82, 136.29, 128.51, 124.69, 124.00, 120.02, 116.91, 104.21, 96.79, 58.68, 45.62

Example 7

Preparation of 4-(2-Diethylamino-ethoxy)-[1,10]phenanthroline-2-carbaldehyde oxime (Compound 10).

1. Synthesis of diethyl-[2-(2-methyl-[1,10]phenanthrolin-4-yloxy)-ethyl]amine

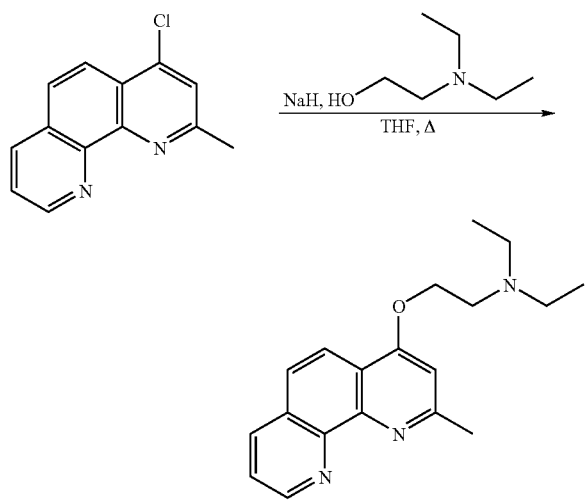

To a suspension of sodium hydride (60% in mineral oil, 5.25 g, 131.1 mmol) in anhydrous THF (90 mL) a solution of N,N-diethyl-2-hydroxyethylamine (15.30 g, 131.1 mmol) in anhydrous THF (60 mL) was slowly added. The mixture was stirred at room temperature for 20 minutes and a solution of 4-chloro-2-methyl-[1,10]phenanthroline (6.00 g, 26.2 mmol) in anhydrous THF (90 mL) was slowly added. The reaction mixture was refluxed for 18 hours and then allowed to cool down to room temperature, quenched with 1N HCl and evaporated. The residue was redissolved in 1N NaOH (150 mL) and extracted with methylene choride (3×200 mL). The combined organic layers were dried (Na$_2$SO$_4$), filtered and concentrated in vacuo. The residue was washed with hexane and purified by flash chromatography (SiO$_2$, MeOH/DCM, 1:40) to yield the pure product as an orange oil (5.1 g, 63%).

2. Synthesis of 4-(2-Diethylamino-ethoxy)-[1,10]phenanthroline-2-carbaldehyde

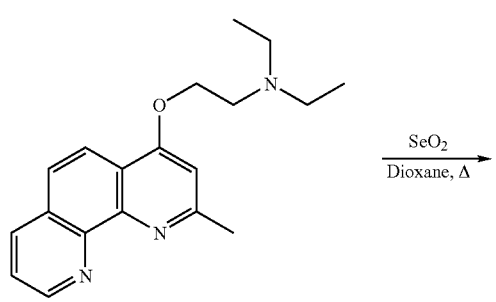

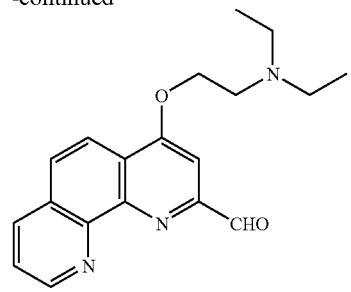

A solution of SeO$_2$ (0.83 g, 7.5 mmol) in a mixture of dioxane (38 mL) and water (3 mL) was heated to reflux in a two-neck 100 mL round-bottomed flask. A solution of diethyl-[2-(2-methyl-[1,10]phenanthrolin-4-yloxy)-ethyl]amine (0.93 g, 3.0 mmol) in hot dioxane (20 mL) was added through an addition funnel over a period of 15 minutes and the reaction mixture was refluxed for 45 minutes. The solvent was evaporated in vacuo and the residue was treated with methylene chloride (100 mL) and saturated NaHCO$_3$ (100 mL). The aqueous layer was extracted with methylene chloride (3×100 mL) and the combined organic layers were washed with brine, dried (Na$_2$SO$_4$), filtered and concentrated. The crude product was purified by flash chromatography (SiO$_2$, MeOH/DCM, 1:40) to afford the pure material as a brown solid (0.19 g, 19%).

3. Synthesis of 4-(2-Diethylamino-ethoxy)-[1,10]phenanthroline-2-carbaldehyde oxime

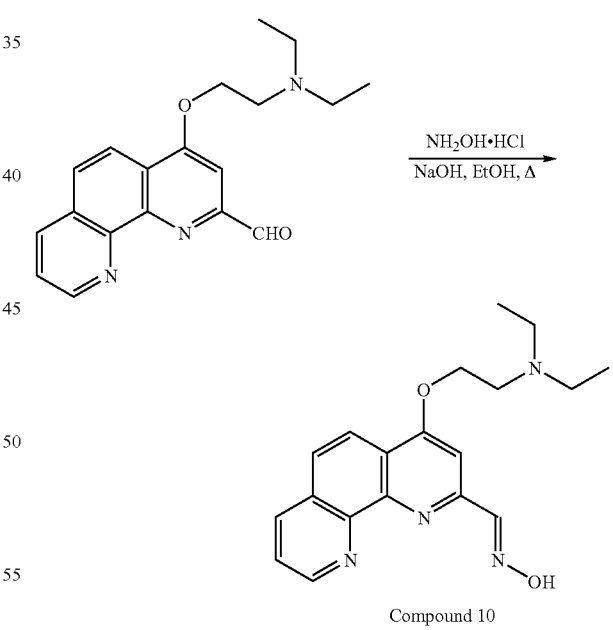

Compound 10

The final step to obtain the Compound 10 is carried out in the same way as described in the synthesis of Compound 4.

$^1$H NMR (DMSO-d$_6$, 400 MHz):

11.85 (s, 1 H); 9.09 (dd, 1 H, J=2.0, 4.4 Hz); 8.46 (dd, 1 H, J=1.0, 8.0 Hz); 8.31 (s, 1 H); 8.13 (d, 1H, J=8.8 Hz); 7.96 (d, 1H, J=8.8 Hz); 7.92 (s, 1H); 7.75 (dd, 1H, J=4.4, 8.0 Hz); 4.36 (t, 2H, J=5.6 Hz); 2.96 (t, 2H, J=5.6 Hz); 2.60 (q, 4H, 7.2 Hz); 1.01 (t, 6H, d=7.2 Hz)

$^{13}$C NMR (DMSO-d$_6$, 100 MHz): 161.0; 153.3; 150.0; 149.6; 146.1; 145.0; 136.2; 128.6; 126.1; 123.3; 120.3; 119.5; 99.3; 67.5; 50.8; 47.1; 12.0

Biology

Example 8

Toxicity

The potential effects on cell viability of the assayed compounds are assayed in SH-SY5Y human neuroblastoma cells, by quantification of Lactate dehydrogenase (LDH) activity release. SH-SY5Y human neuroblastoma cells are seeded into 96-well culture plates at 104 cells/well. The medium is then removed and the cells incubated with different concentrations of the compounds during 24 h. The compounds are tested at increasing concentrations starting from 1 μM, in fresh culture medium, in order to find the minimum concentration at which the compounds are toxic, up to a maximum of 1 mM. After 24 h, the medium is removed and cells attached to the bottom of the well are lysed by adding 50 μl of Krebs-Hepes; Triton X-100 1% during 5 minutes at room temperature. For LDH release quantification, the Roche cytotoxicity detection kit (Cat. No. 11 644 793 001) is used. The LDH activity is measured by its absorbance at 492 nm with reference wavelength 620 nm.

In Table 1, for each compound the maximum concentration at which toxicity was tested is indicated in the second column. In the third column, it is indicated whether at this maximum concentration the compound was toxic or not. All the compounds, with the exception of Compound 3, resulted non-toxic at the concentration for which activity was found, in most of the cases even at a 1000-fold concentration. Thus, the compounds may be considered non-toxic.

TABLE 1

| Compound No. | Maximum concentration tested for toxicity | Yes/No |
| --- | --- | --- |
| Compound 1 | 1 mM | Yes |
| Compound 2 | 1 mM | Yes |
| Compound 3 | 10 μM | Yes |
| Compound 4 | 1 mM | Yes |
| Compound 5 | 1 mM | Yes |
| Compound 6 | 1 mM | Yes |
| Compound 7 | 1 mM | Yes |
| Compound 8 | 1 mM | No |
| Compound 9 | 10 μM | No |
| Compound 10 | 1 μM | Yes |
| Compound 12 | 1000 μM | No |
| Compound 13 | 1000 μM | No |
| Compound 14 | 1000 μM | Yes |
| Compound 15 | 100 μM | Yes |
| Compound 16 | 10 μM | Yes |
| Compound 17 | 1000 μM | Yes |
| Compound 18 | 10 μM | Yes |
| Compound 19 | 10 μM | Yes |
| Compound 20 | 10 μM | Yes |

Example 9

Protection Against Hydrogen Peroxide-Induced Cell Eeath

The aim of this assay is to determine the neuroprotective effect of the compounds of formula (I), when human neuroblastoma cells are exposed to oxidative stress induced by hydrogen peroxide, which is highly deleterious to the cell and its accumulation causes oxidation of cellular targets such as DNA, proteins, and lipids leading to mutagenesis and cell death.

SH-SY5Y human neuroblastoma cells are seeded into 96-well culture plate at a density of 104 cells/well. Cells are exposed to different concentrations of the compound one hour before the treatment with $H_2O_2$ 100 μM during 24 h. 5 mM N-acetylcysteine (NAC), a known anti-oxidant agent was used as a positive control, and preincubated 1 hour before the treatment with $H_2O_2$. After 24 h, the medium is removed and cells attached to the bottom of the well are lysed by adding 50 μl of Triton X-100 1% in Krebs-Hepes during 5 minutes at room temperature. For LDH release quantification, Roche cytotoxicity detection kit (Cat. No. 11 644 793 001) was used.

The minimum concentration of Compounds 1-10 for which protection against $H_2O_2$ was determined are shown in Table 2.

TABLE 2

| Compound No. | Protect. $H_2O_2$ |
| --- | --- |
| Compound 1 | 0.05 μM |
| Compound 2 | 0.05 μM |
| Compound 3 | 10 μM |
| Compound 4 | 0.05 μM |
| Compound 5 | 5 nM |
| Compound 6 | 5 nM |
| Compound 7 | 0.05 μM |
| Compound 8 | 50 nM |
| Compound 9 | 5 μM |
| Compound 10 | 50 nM |
| Compound 12 | 0.1 μM |
| Compound 13 | 0.5 μM |
| Compound 14 | 0.05 μM |
| Compound 15 | 0.5 μM |
| Compound 16 | 0.05 μM |
| Compound 17 | 5 μM |
| Compound 18 | 0.05 μM |
| Compound 19 | 0.5 μM |
| Compound 20 | 0.5 μM |

Protection Against 6-OHDA-Induced Cell Death

The aim of this experiment is to determine the protective effect of the compounds of formula (1) against the toxicity caused by 6-OHDA. This toxin induces a cell death similar to which occurs in Parkinson's disease, destroying dopaminergic neurons ("MPTP and 6-hydroxydopamine-induced neurodegeneration as models for Parkinson's disease: neuroprotective strategies"; Grunblatt E, et al.; J Neurol. 2000 Apr; 247 Suppl 2:II95-102).

Two or three days before the experiment, the SH-SY5Y human neuroblastoma cells are seeded into 96-well culture plate at a density of $10^4$ cells/well. Cells are exposed to the treatment with 6-OHDA and, finally, cell death is measured by LDH quantification. As positive control we used NAC.

The assay is performed in two different experimental conditions:

Example 10

A) NAC and the compound of formula (I) are preincubated during 2 hours before the treatment with 6-OHDA 75 μM during 16 hours. The assay is performed in medium containing 10% Foetal bovine serum.

The neuroprotective results against cellular death induced by 6-OHDA are shown in Table 3. For each compound the minimum concentration of compound of formula (I) at which a neuroprotective effect is shown.

TABLE 3

| Compound No. | Protect. 6-OHDA (+ FBS) |
|---|---|
| Compound 1 | 0.5 μM |
| Compound 2 | 0.5 μM |
| Compound 4 | 0.05 μM |
| Compound 5 | 0.05 μM |
| Compound 6 | 0.05 μM |
| Compound 7 | 0.05 μM |
| Compound 8 | 0.05 μM |
| Compound 9 | 5 μM |
| Compound 10 | 0.05 μM |
| Compound 12 | 0.1 μM |
| Compound 13 | 0.5 μM |
| Compound 14 | 0.5 μM |
| Compound 16 | 0.5 μM |
| Compound 18 | 0.05 μM |

Example 11

B) NAC and the compound of formula (I) are preincubated during 1 hour before the treatment with 6-OHDA 50 μM during 24 hours. The assay is performed in a medium without any fetal bovine serum.

The neuroprotective results against cellular death induced by 6-OHDA are shown in Table 4. For each compound the minimum concentration of compound of formula (I) at which a neuroprotective effect is shown.

TABLE 4

| Compound No. | Protect. 6-OHDA (−FBS) |
|---|---|
| Compound 1 | 0.5 μM |
| Compound 2 | 0.5 μM |
| Compound 3 | 10 μM |
| Compound 4 | 0.5 μM |
| Compound 5 | 0.5 μM |
| Compound 6 | 0.5 μM |
| Compound 7 | 0.5 μM |
| Compound 8 | 0.5 μM |
| Compound 9 | 5 μM |
| Compound 10 | 0.5 μM |
| Compound 12 | 0.5 μM |
| Compound 13 | 5 μM |
| Compound 14 | 0.5 μM |
| Compound 16 | 10 μM |
| Compound 18 | 10 μM |

Example 12

Neuroprotection Against Aβ Toxicity

In order to evaluate potential neuroprotection of compounds, SH-SY5Y cells, cultured in 96-well plates, were pre-treated for 1 hour with the compound at different concentrations and then exposed 24 hours to 200 μM Aβ$_{25-35}$ (Neosystem) to induce extensive oxidative stress and cell death. The ability of the compound of protecting against this toxicity is then evaluated by measuring intracellular LDH, using the colorimetric LDH assay.

It is widely accepted that the neurotoxic activity of Aβ resides within amino acids 25-35 (see e.g. Yankner B A et al., (1990) Neurotrophic and neurotoxic effects of amyloid β protein: reversal by tachykinin neuropeptides; Science 250: 279-282).

In Table 5, the minimum concentration at which the tested compounds showed neuroprotection against Aβ$_{25-35}$ toxicity is shown.

TABLE 5

| Compound No. | Protect. beta-Amyloid$_{25-35}$ |
|---|---|
| Compound 1 | 5 μM |
| Compound 2 | 10 μM |
| Compound 4 | 0.5 μM |
| Compound 6 | 10 μM |
| Compound 8 | 0.5 μM |
| Compound 9 | 5 μM |
| Compound 10 | 0.5 μM |
| Compound 12 | 10 μM |
| Compound 13 | 5 μM |
| Compound 14 | 10 μM |
| Compound 16 | 5 μM |
| Compound 18 | 10 μM |

Example 13

Inhibition of Aβ(1-40) Secretion

To quantitate Aβ secretion ELISA-based method was used. The assay consists in detection of antigen by selective monoclonal anti-Aβ-antibodies at two different epitopes forming a "Sandwich-complex", that is detected by colorimetric measure due to the binding of a secondary antibody conjugated with peroxidase that catalyses the conversion of a substrate or chromogen, TMB, into a coloured product, directly proportional to the peptide quantity in the sample. The Aβ production has been analyzed by ELISA, using a colorimetric commercial kit: Immunoassay Kit Human β Amyloid 1-40 (Biosource).

Aβ (1-40) were quantified from cellular supernatants. An APP-transfected cell line has been employed for the experiments: CHO7W (stably transfected with human APP$_{751}$ wt cDNA). The cells were grown in a culture medium consisting of DMEM supplemented with 2% Fetal bovine serum, 1% penicillin-streptomycin, 1% L-glutamine and 200 μg/ml G418. Cells are seeded in 96-well culture microplate, at 5000 cells/well and treatment with different compounds at different concentrations is performed 24 hour after seeding.

OM99-2 (H-5108, Bachem), a BACE inhibitor, was used as Aβ secretion reduction positive control in all the Aβ secretion studies. The cells were treated with this compound at 3 μM concentration, culture media were collected at 24 hours. At this concentration OM99-2 shows a percentage of Aβ release inhibition between 20 and 60%.

In Table 6 the minimum concentration for each tested compound at which the compound inhibits beta-amyloid inhibition is shown.

TABLE 6

| Compound No. | Inhibition secretion beta-amyloid |
|---|---|
| Compound 1 | 0.01 mM |
| Compound 2 | 1 mM |
| Compound 4 | 0.05 mM |
| Compound 5 | 1 nM |
| Compound 6 | 10 nM |
| Compound 7 | 1 nM |

TABLE 6-continued

| Compound No. | Inhibition secretion beta-amyloid |
|---|---|
| Compound 8 | 1 mM |
| Compound 9 | 10 mM |
| Compound 10 | 1 mM |
| Compound 12 | 1 μM |
| Compound 13 | 10 μM |
| Compound 14 | 0.01 μM |
| Compound 15 | 10 μM |
| Compound 16 | 1 μM |
| Compound 17 | 10 μM |
| Compound 18 | 0.1 μM |
| Compound 19 | 1 μM |
| Compound 20 | 10 μM |

Example 14

Screening Pharmacokinetic Study.

The objective of this study is to evaluate the oral bioavailability and the plasmatic and brain pharmacokinetic parameters after oral and intravenous administration, thus determining if compounds of formula (I) are able to cross the blood brain barrier (BBB). In order to measure the levels of compounds of formula (I) in plasma and brain, mice (C57BL6/J, males of 8-week aged) were dosed with an intravenous administration (1 mg/kg) and two oral administrations (20 mg/kg and 200 mg/kg) of the different compounds. Each compound was solved in appropriate excipients. In the case of oral administration, compound was administered by means of an oral gavage coupled to a syringe. In the intravenous administration animals, the test item was administered by a single injection with a syringe coupled to a 30 G needle.

Two animals were sacrificed (according to internal SOPs and following animal handling and welfare guidelines) at each selected extraction times (i.e. 30 min, 1 h, 2 h, 4 h, 6 h, 8 h and 24 hours after administration), and from each animal, both brain and blood samples were obtained. Plasma was extracted by centrifugation of the blood samples. Each sample time represents two male mice from which samples were obtained.

The method for the analysis of plasma and brain samples involved isolation of the analyte from the biological matrix by protein precipitation or solid-phase extraction followed by analysis using LC-MS/MS. Limits of quantification for these compounds were in the order of 2-10 ng/mL. The software Winnonlin professional version 5.2 was used for the calculation of pharmacokinetic parameters.

Results

In the following tables, the abbreviations have the meaning indicated below:

AUC=Area under the curve $T_{1/2}$=Half-life $T_{max}$=the time after administration of a drug when the maximum plasma concentration is reached; when the rate of absorption equals the rate of elimination $C_{max}$=maximum plasma concentration of the drug V. Adm. and Vol. Adm.=volume of administration 1. Group 1-2 mg/kg Intravenous Route

TABLE 7

| Compound No. | V. Adm. (ml/Kg) | Dose (mg/Kg) | $C_{max}$ Plasma (ng/ml) | $T_{1/2}$ (h) | $T_{max}$ | AUC |
|---|---|---|---|---|---|---|
| Compound 4 | 2 | 1.00 | 78.70 | 0.22 | 0.25 | 36 |
| Compound 7 | 1 | 1.20 | 104.2 | 4.47 | 1.00 | 319 |
| Compound 8 | 2 | 1.00 | 689.5 | 1.11 | 0.25 | 243.7 |
| Compound 10 | 2 | 2.00 | 136.50 | 8.10 | 0.08 | 148 |

TABLE 8

| Compound No. | Dose (mg/Kg) | $C_{max}$ Brain (ng/g) | $T_{1/2}$ (h) | $T_{max}$ | AUC | % $C_{max}$ | % AUC |
|---|---|---|---|---|---|---|---|
| Compound 4 | 1.00 | 104.40 | 0.39 | 0.25 | 45.80 | 132.66 | 127.22 |
| Compound 7 | 1.20 | 386.10 | NC | 0.08 | 330.50 | 370.54 | 103.61 |
| Compound 8 | 1.00 | 36.10 | 0.18 | 0.25 | 10.70 | 5.24 | 4.39 |
| Compound 10 | 2.00 | 18.7 | 2.60 | 0.08 | 33.90 | 13.70 | 22.91 |

2. Group 20 mg/kg Oral Route

TABLE 9

| Compound No. | V. Adm. (ml/Kg) | $C_{max}$ Plasma (ng/ml) | $T_{1/2}$ (h) | $T_{max}$ | AUC | Bioavailability |
|---|---|---|---|---|---|---|
| Compound 4 | 4 | 20.75 | 0.30 | 0.25 | 7.24 | 1.01 |
| Compound 7 | 4 | 106.50 | 1.66 | 0.30 | 378.10 | 7.11 |
| Compound 8 | 4 | 396.40 | 3.90 | 0.25 | 325.20 | 6.67 |
| Compound 10 | 4 | 149.20 | 4.00 | 1.00 | 184.40 | 12.46 |

TABLE 10

| Compound No. | Dose (mg/g) | $C_{max}$ Brain (ng/g) | $T_{1/2}$ (h) | $T_{max}$ | AUC | % $C_{max}$ | % AUC |
|---|---|---|---|---|---|---|---|
| Compound 4 | 20 | 15.40 | 0.66 | 0.25 | 20.00 | 74.22 | 276.24 |
| Compound 7 | 20 | 19.62 | 0.73 | 4.00 | 23.90 | 41.66 | 27.76 |
| Compound 8 | 20 | 24.60 | 1.80 | 0.25 | 13.60 | 6.21 | 4.18 |
| Compound 10 | 20 | 13.07 | NC | 1.00 | 22.00 | 8.76 | 11.93 |

3. Group 200 mg/kg Oral Route

TABLE 11

| Compound No. | Vol. Adm. (ml/Kg) | $C_{max}$ Plasma (ng/ml) | $T_{1/2}$ (h) | $T_{max}$ | AUC | Bioavailability |
|---|---|---|---|---|---|---|
| Compound 4 | 4 | 930.70 | 0.92 | 0.50 | 1375.70 | 19.11 |
| Compound 7 | 4 | 1205.20 | — | 0.50 | 1696.80 | 3.19 |

TABLE 11-continued

| Compound No. | Vol. Adm. (ml/Kg) | $C_{max}$ Plasma (ng/ml) | $T_{1/2}$ (h) | $T_{max}$ | AUC | Bioavail-ability |
|---|---|---|---|---|---|---|
| Compound 8 | — | — | — | — | — | — |
| Compound 10 | 4 | 3950.70 | 3.79 | 0.50 | 11478.90 | 77.56 |

TABLE 12

| Compound No. | Dose (mg/g) | $C_{max}$ Brain (ng/g) | $T_{1/2}$ (h) | $T_{max}$ | AUC | % $C_{max}$ | % AUC |
|---|---|---|---|---|---|---|---|
| Compound 4 | 200 | 1394.40 | 0.94 | 0.50 | 1537.90 | 149.82 | 111.79 |
| Compound 7 | 200 | — | — | — | — | — | — |
| Compound 8 | 200 | — | — | — | — | — | — |
| Compound 10 | 200 | 7751.80 | — | 2.00 | 95478.00 | 196.21 | 831.77 |

Conclusions.

Regarding the results shown in previous tables (7-12), all tested compounds of formula (I) are able to cross the blood brain barrier because they are detected in brain. Oral bioavailability is in the range between 7 and 10% at low dose, and is increased significantly at the high concentration.

Example 15

Evaluation of the Chelating Ability of some Compounds of Formula (I) with Fe(II)

The assays carried out in presence of the chelating ligands Compound 4, Compound 7, Compound 8 and compound 10 demonstrated that the ligands are able to complex the Fe (II), as the spectrum obtained for the mixture of each ligand and the iron differs from the sum of the respective individual spectra (see FIGS. 2, 3, 4 and 5).

Example 16 a) Evaluation of the Chelating Ability of some Compounds of Formula (I) with Fe (III)

The assays carried out in presence of Fe (III) have demonstrated that none of the compounds of formula (I) were able to complex this metal, because no change in the absorbance spectra of the ligand in presence of Fe (III) is observed; as shown in FIG. 1 for compounds 4, 7, 8 and 10. Only one line is observed, as the spectra are overlapping (see FIG. 1).

b) Evaluation of the Chelating Ability of some Compounds of Formula (I) with Cu (II)

Figure 6:
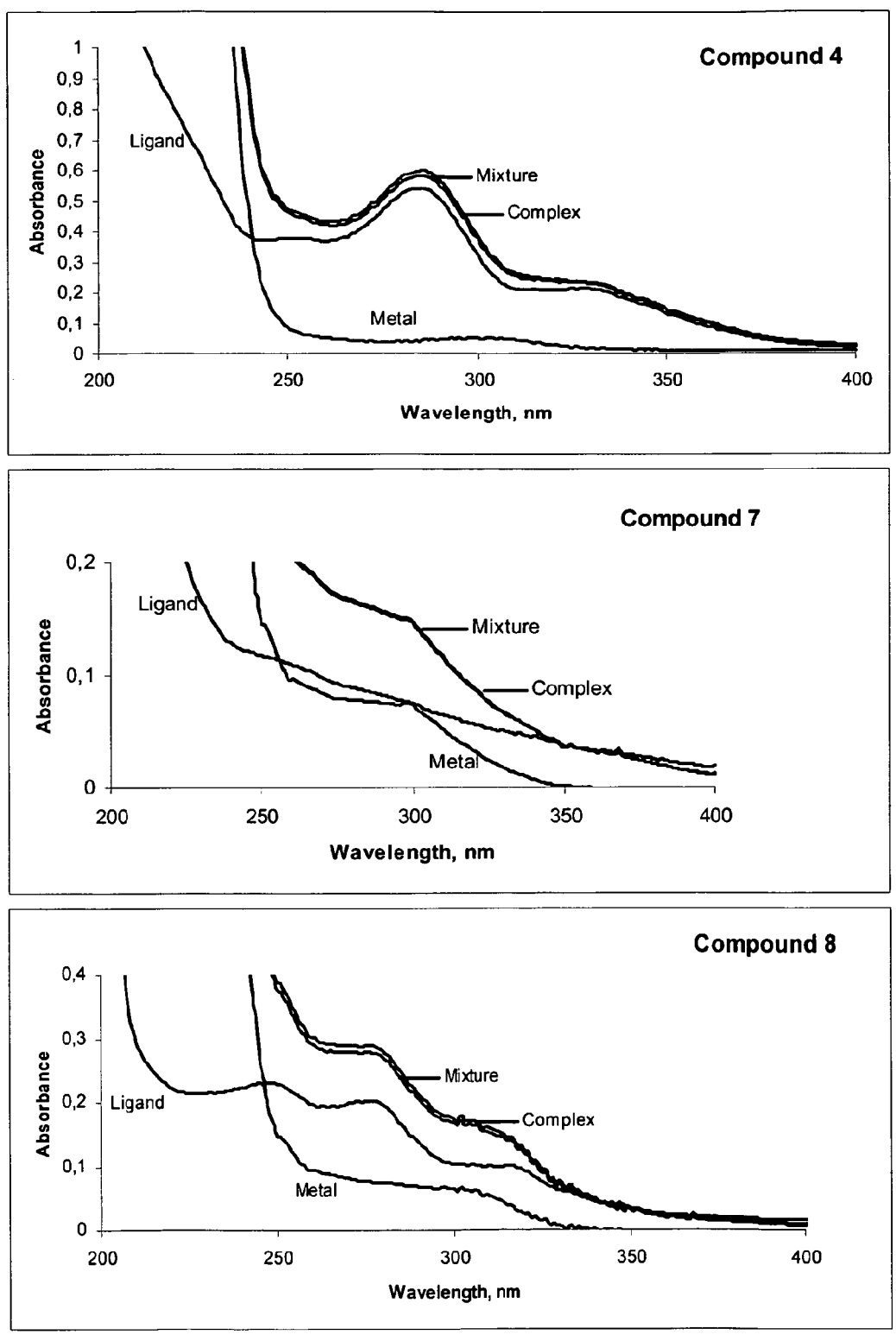
FIG. 6 depicts the absorbance spectra of the mixture of Cu (II) and each of the quelating ligands (Compound 4, Compound 7, Compound 8). Concentration of Cu(II) and all compounds 200 µM, PBS 10 mM, pH 7.4.
Figure 7:
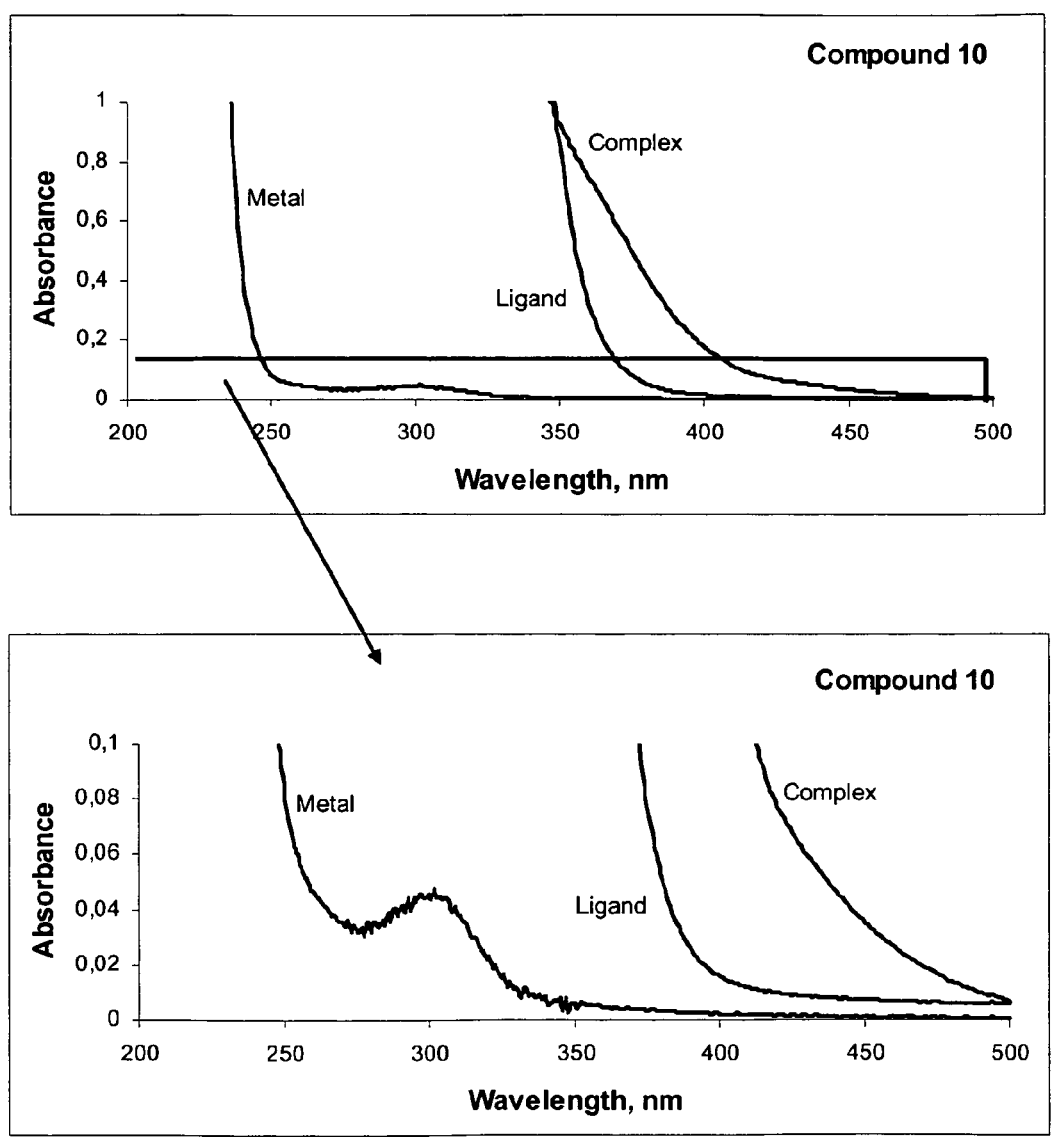
FIG. 7 is the absorbance spectra of the complex Cu(II)-Compound 10. Concentration 200 µM, PBS 10 mM, pH 7.4.
Figure 8:
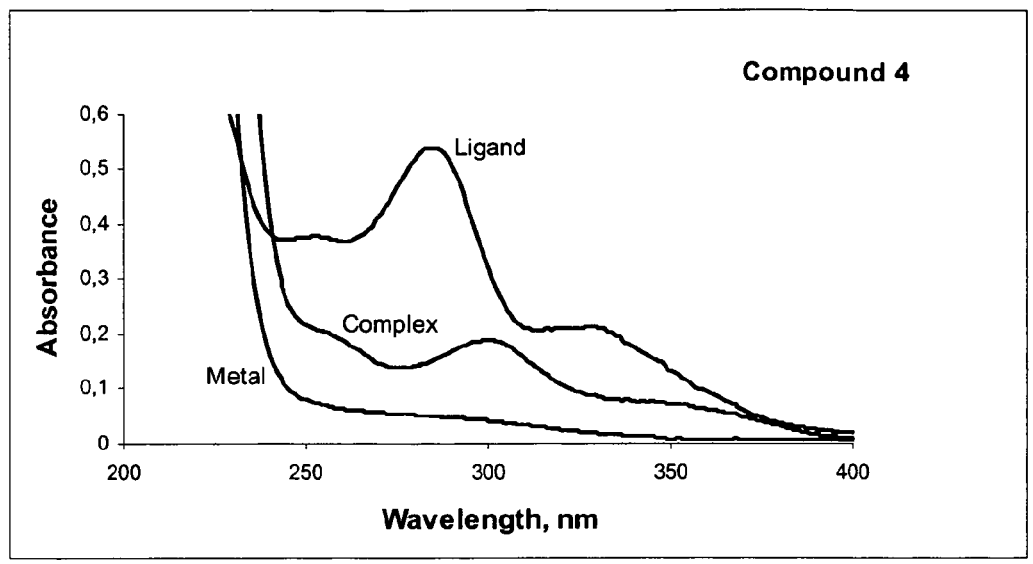
FIG. 8 represents the absorbance spectra of the complex Zn(II)-Compound 4. Concentration 200 µM, PBS 10 mM, pH 7.4.
Figure 9:
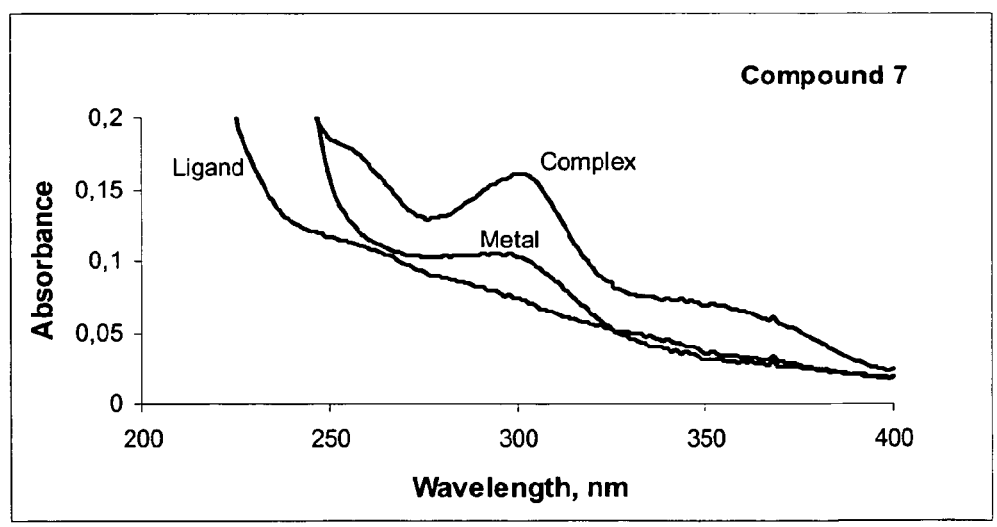
FIG. 9 shows the absorbance spectra of the complex Zn(II)-Compound 7. Concentration 180 µM, PBS 10 mM, pH 7.4.
Figure 10:
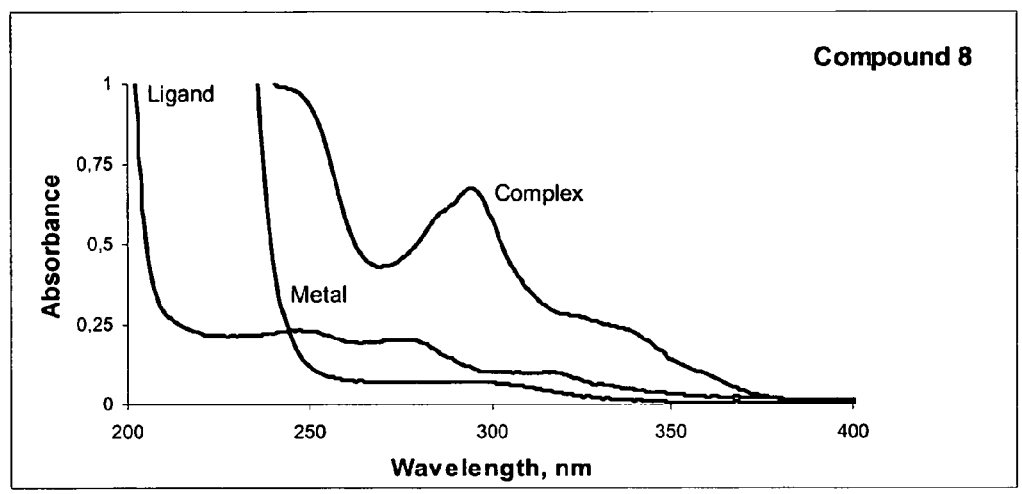
FIG. 10 shows the absorbance spectra of the complex Zn(II)-Compound 8. Concentration 100 µM, PBS 10 mM, pH 7.4.
Figure 11:
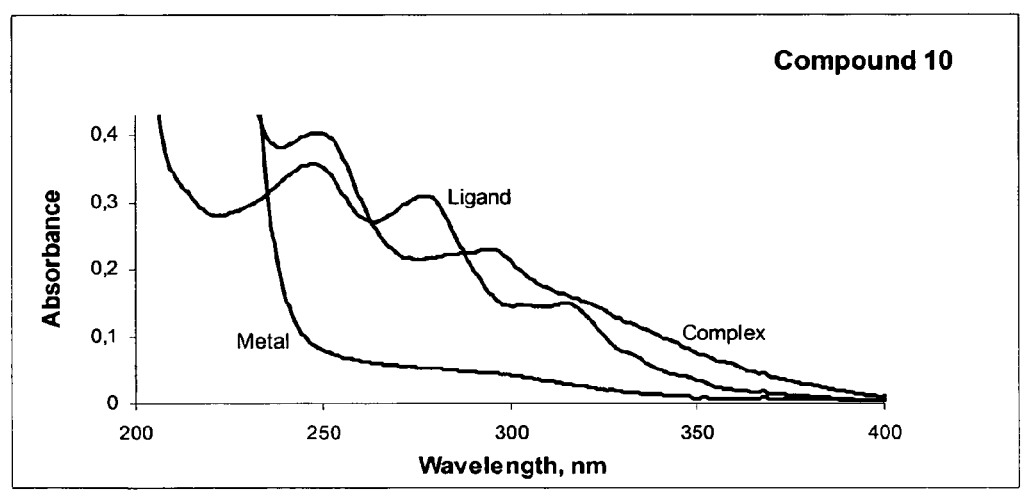
FIG. 11 shows the absorbance spectra of the complex Zn(II)-Compound 10. Concentration 20 µM, PBS 10 mM, pH 7.4.

The assays carried out in presence of the chelating ligands Compound 4, Compound 7 and Compound 8 demonstrated that none of the ligands are able to complex the Cu (II), as the spectrum obtained for the mixture of each ligand and the copper is coincident with the sum of the respective individual spectra (see FIGS. 6 and 7).

c) Evaluation of the Chelating Ability of some Compounds of Formula (I) with Zn (II)

All of compounds 4, 7, 8, and 10 complexed with Zn(II) to an extent, but having a relatively low formation constant and a relatively high dissociation grade, thus showing that the complexes are not too stable (see FIGS. 8, 9,10 and 11).

Summary of the Results

In the formation of complexes between metalic ions and quelatns, the higher a formation constant and the lower the dissociation grade, the more stable is the complex. Therefore, it may be observed that the compounds of formula (I) have a high affinity to Fe (II) in comparison to the rest of metalic ions tested.

TABLE 13

| Metal | Ligand (compound no.) | Expecting time | pH | Stoichiometry | Dissociation grade | Formation constant | ε approx. (l mol$^{-1}$ cm$^{-1}$) |
|---|---|---|---|---|---|---|---|
| Cu (II) | 10 | 2 h | 7.4 | 1:1 (ML) | 3.8 ± 0.4 | 4.4 ± 0.6 · 10$^6$ (l/mol) | 400 |
| Zn (II) | 4 | 24 h | 7.4 | 1:1 (ML) | 46 ± 7 | 2.2 ± 0.6 · 10$^4$ (l/mol) | 1000 |
|  | 7 | 24 h | 7.4 | 1:2 (ML$_2$) | 13.4 ± 0.7 | 2.2 ± 0.6 · 10$^{10}$ (l$^2$/mol$^2$) | 840 |
|  | 8 | 4 h | 7.4 | 1:2 (ML$_2$) | 7.7 ± 0.6 | 1.4 ± 0.6 · 10$^{11}$ (l$^2$/mol$^2$) | 7100 |
|  | 10 | 4 h | 7.4 | 1:2 (ML$_2$) | 3.7 ± 0.6 | 1.7 ± 0.4 · 10$^{13}$ (l$^2$/mol$^2$) | 9400 |
| Fe (II) | 4 | 30 min | 8* | 1:3 (ML$_3$) | 0.147 ± 0.002 | 8.2 ± 0.5 · 10$^{12}$ | 1.8 · 10$^3$ |
|  | 7 | 60 min | 8* | 1:3 (ML$_3$) | 0.023 ± 0.002 | 2.0 ± 0.6 · 10$^{15}$ | 2.8 · 10$^2$ |
|  | 8 | Immediate | 7.4 | 1:3 (ML$_3$) | 0.022 ± 0.006 | 4.0 ± 1.3 · 10$^{17}$ | 1.6 · 10$^3$ |
|  | 10 | Immediate | 7.4 | 1:3 (ML$_3$) | 0.019 ± 0.004 | 5.0 ± 1.0 · 10$^{17}$ | 6.7 · 10$^3$ |

The invention claimed is:

1. A compound of formula (I):

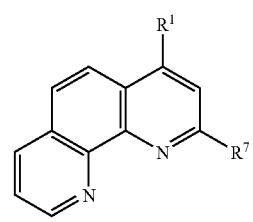

(I)

wherein $R^1$ is —S—$R^3$;

$R^7$ is selected from —CH=N—O$R^8$ or —CHO;

R³ is selected from the group consisting of C₆-C₁₅ aryl and heteroaryl, each of which is optionally substituted by C₁-C₆ alkyl, C₆-C₁₅ aryl, halogen, —(C=O)NR⁵R⁶, —(C=O)OR⁵, C₁-C₆ alkoxy and/or —NR⁵R⁶, R⁵ and R⁶ being independently selected from hydrogen and C₁-C₆ alkyl, R⁸ is selected from hydrogen and C₁-C₆ alkyl;

or any salt or stereoisomer or tautomer thereof.

2. The compound according to claim 1, wherein R⁷ is —CH=N—OR⁸.

3. The compound according to claim 2, wherein R⁸ is hydrogen.

4. The compound according to claim 1, wherein R³ is selected from heteroaryl and heteroaryl substituted by C₁-C₆ alkyl, C₆-C₁₅ aryl, halogen, —(C=O)NR⁵R⁶, —(C=O)OR⁵, C₁-C₆ alkoxy and/or —NR⁵R⁶.

5. The compound according to claim 4, wherein the heteroaryl group is substituted by C₁-C₃ alkyl.

6. The compound according to claim 1, wherein the double bond of the oxime group —CH=NOR⁸ presents an E conformation.

7. The compound according to claim 1, wherein R⁷ is —CH=N—OR⁸ and R¹ is —S—R³.

8. The compound according to claim 1, selected from 4-(Thiazol-2-ylsulfanyl)-[1,10]phenanthroline-2-carbaldehyde oxime 4-(5-Methyl-thiazol-2-ylsulfanyl)-[1,10]phenanthroline-2-carbaldehyde oxime 4-(5-Methyl-[1,3,4]thiadiazol-2-ylsulfanyl)-[1,10]phenanthroline-2-carbaldehyde oxime 4-([1,3,4]Thiadiazol-2-ylsulfanyl)-[1,10]phenanthroline-2-carbaldehyde oxime and salts, stereoisomers and tautomers thereof.

9. A pharmaceutical composition comprising at least one compound according to claim 1, and at least one pharmaceutically acceptable carrier.

10. A process for the preparation of the compound of claim 1, comprising the steps of:

a) optionally reacting a compound of formula (III) with a sodium salt of the corresponding alkoxide or thiolate, to form a compound of formula (II);

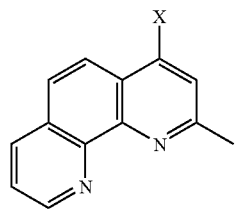

(III)

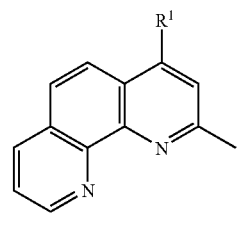

(II)

wherein
X is an halogen;
R¹ is —S—R³;

R³ is selected from the group consisting of
C₆-C₁₅ aryl and heteroaryl, each of which is optionally substituted by C₁-C₆ alkyl, C₆-C₁₅ aryl, halogen, —(C=O)NR⁵R⁶, —(C=O)OR⁵, C₁-C₆ alkoxy and/or —NR⁵R⁶;

b) oxidizing the methyl group of the compound of formula (II) with an oxidizing agent to form a compound of formula (I);

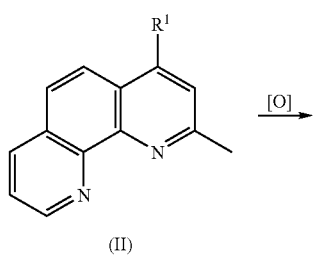

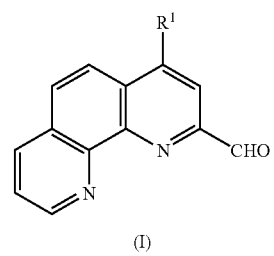

wherein R¹ is as defined in step a); and, optionally c) converting the aldehyde group —CHO in the compound of formula (I) into an oxyme group —CH=N—OR⁸, wherein R⁸ is selected from hydrogen and C₁-C₆ alkyl, in the presence of hydroxylamine or O—(C₁-C₆)alkylhydroxylamine:

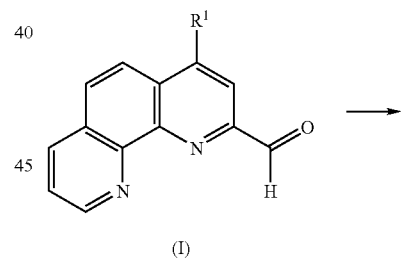

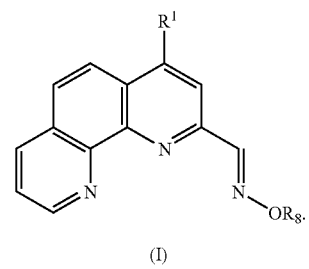

11. A biological assay method, comprising reacting the compound of claim 1 with a biological sample.

12. A method of inhibiting secretion of amyloid beta, which method comprises administering to a patient in need thereof a therapeutically effective amount of at least one compound according to claim 1.

* * * * *